United States Patent
Bowman et al.

[11] Patent Number: 6,068,612
[45] Date of Patent: *May 30, 2000

[54] AIR DETECTOR

[75] Inventors: George Bowman, Vernon Hills; Joseph Matthews, Grayslake, both of Ill.; Kurt Eyster, Santa Barbara, Calif.

[73] Assignee: Baxter International Inc., Deerfield, Ill.

[*] Notice: This patent is subject to a terminal disclaimer.

[21] Appl. No.: 09/113,765

[22] Filed: Jul. 10, 1998

Related U.S. Application Data

[62] Division of application No. 08/629,879, Apr. 10, 1996, Pat. No. 5,843,035.

[51] Int. Cl.[7] .................................................... A61M 1/00
[52] U.S. Cl. ........................... 604/122; 604/123; 604/65
[58] Field of Search ........................ 604/65–67, 131, 604/122, 123; 128/DIG. 12, DIG. 13

[56] References Cited

U.S. PATENT DOCUMENTS 4,821,558   4/1989   Pastrone et al. ......................... 73/19
4,882,575  11/1989   Kawahara ............................... 340/608
5,176,631   1/1993   Koenig .................................... 604/65

*Primary Examiner*—Corrine McDermott
*Assistant Examiner*—Cris L. Rodriguez
*Attorney, Agent, or Firm*—Paul E. Schaafsma; Francis C. Kowalik

[57] ABSTRACT

The present invention provides an apparatus for detecting excessive air in a liquid flow-through tube. The apparatus includes an ultrasonic transmitter for transmitting ultrasonic signals and an ultrasonic receiver for receiving ultrasonic signals. The ultrasonic transmitter and ultrasonic receiver are separated by the IV tube. The apparatus further provides circuit means for generating at least two transmitting signals to actuate the ultrasonic transmitter and circuit means for detecting received signals. Means are provided for determining whether the received signal is indicative of air or liquid in the IV tube. The apparatus further relies on logarithmic detection of air in fluids rather than linear detection which provides a larger safety factor in prediction of air embolus.

8 Claims, 22 Drawing Sheets

AIR DETECTOR

This application is a division of application Ser. No. 08/629,879, filed Apr. 10, 1996, now U.S. Pat. No. 5,843,035.

FIELD OF THE INVENTION

The present invention relates to medical infusion pump air detectors.

BACKGROUND OF THE INVENTION

The administration of intravenous medical fluids to a patient is well known in the art. Typically, a solution such as saline, glucose or electrolyte contained in a glass or flexible container is fed into a patient's venous system through a conduit such as a polyvinyl chloride (PVC) intravenous (IV) tube which is accessed to the patient by a catheter. Many times, the fluid is infused under the forces of gravity, and the rate of flow is controlled by a roller clamp which is adjusted to restrict the flow lumen of the IV tube until the desired flow rate is obtained.

Flow from the container to the patient also is known to be regulated by means other than a roller clamp. It is becoming more and more common to use an electronically controlled infusion pump. Such pumps include, for example, peristaltic-type pumps and valve-type pumps. Peristaltic-type pumps typically include an array of cams angularly spaced from each other which drive cam followers connected to pressure fingers. These elements cooperate to impart a linear wave motion on the pressure fingers. This linear wave motion is used to apply force to the IV tube, which imparts the motion to the fluid in the IV tube thereby propelling the fluid. An alternative type of peristaltic pump employs a plurality of roller members which roll over the IV tube to impart the motion to the fluid in the IV tube. Infusion pumps also employ pumping chambers having upstream and downstream valves to sequentially impart the propulsion to the fluid. Such valve-type pumps typically require the use of a specialized pumping cassette chamber, which is contained on a dedicated IV tube between the patient and the source of fluid.

A particular concern in infusing a patient with medical fluid is that air will be introduced into the IV tube, which can then be infused into the patient's venous system. Prior art pumps have employed air detectors designed to detect the presence of air in the IV tube. Such air detectors, however, have had a relatively small dynamic range for testing, which has made such testing sensitive to the type of IV tube utilized and the temperature of the pump environment.

What is needed is an air sensor for a medical infusion pump which has a large dynamic range for testing, so that positive delineation is possible under a wide range of IV tubes and reasonable temperature extremes. It would be advantageous for such a sensor not only to sense air in an IV tube, but also to discriminate between an empty IV tube and no IV tube. It would be further advantageous for such an air sensor to have a miniature size capable of being employed while minimally adding size and weight to the pump housing. It would be further advantageous for such an air sensor to use low power consumption so that, when the pump is operating on auxiliary battery power, battery life is extended.

SUMMARY OF THE INVENTION

The present invention provides an air sensor for a medical infusion pump which has a large dynamic range for air and no-air testing, so that positive delineation is possible under all IV tubes and reasonable temperature extremes. The present invention is capable of discriminating between an empty IV tube and no IV tube. The present invention provides for such an air sensor to have a miniature size capable of being employed while minimally adding size and weight to the pump housing. The present invention provides for such an air sensor to use low power consumption so that, when the pump is operating on auxiliary battery power, the battery life is extended.

The present invention provides an apparatus for detecting excessive air in a liquid flow-through tube. The apparatus includes an ultrasonic transmitter for transmitting ultrasonic signals and an ultrasonic receiver for receiving ultrasonic signals. The ultrasonic transmitter and ultrasonic receiver are separated by the IV tube. The apparatus further provides circuit means for generating at least two transmitting signals to actuate the ultrasonic transmitter and circuit means for detecting received signals. Means are provided for determining whether the received signal is indicative of air or liquid in the IV tube or no IV tube.

The apparatus further relies on logarithmic detection of air in fluids rather than linear detection which provides a larger safety factor in prediction of air embolus. The apparatus further includes sharp filter responses that discriminate against ambient interference. The apparatus further provides an improved acoustic mechanism to detect the delineation between air and water better than air sensors of the prior art. The apparatus further utilizes the "dual mode" properties of ultrasonic crystals such that the "thickness mode" at a first frequency is used to detect air in tubes while the "radial mode" at a second frequency is used to detect the presence or absence of the tube and permit the detection of micro droplets in the tube.

DETAILED DESCRIPTION OF A PREFERRED EMBODIMENT

Figure 1:
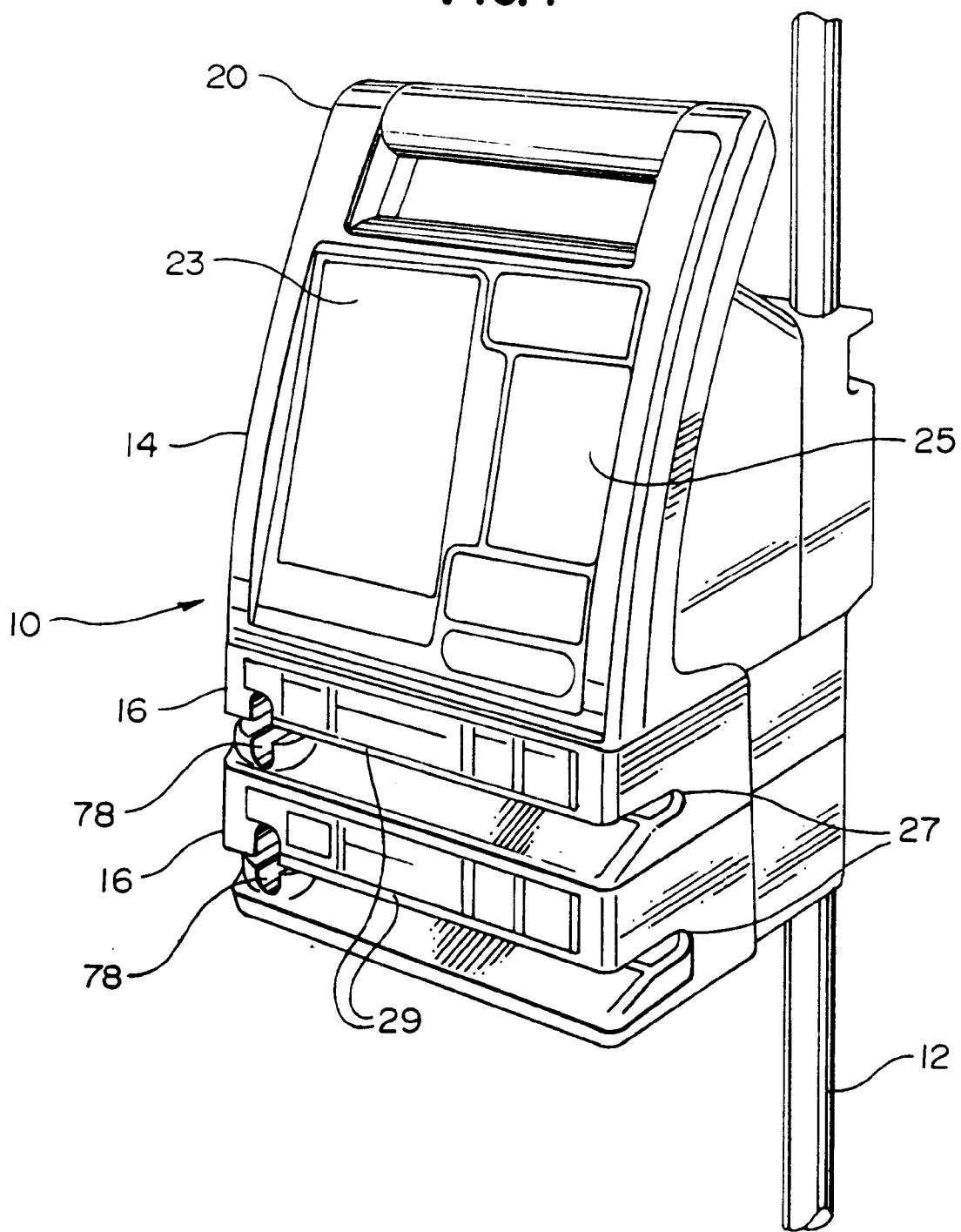
FIG. 1 is a perspective view of an infusion pump.
Figure 2:
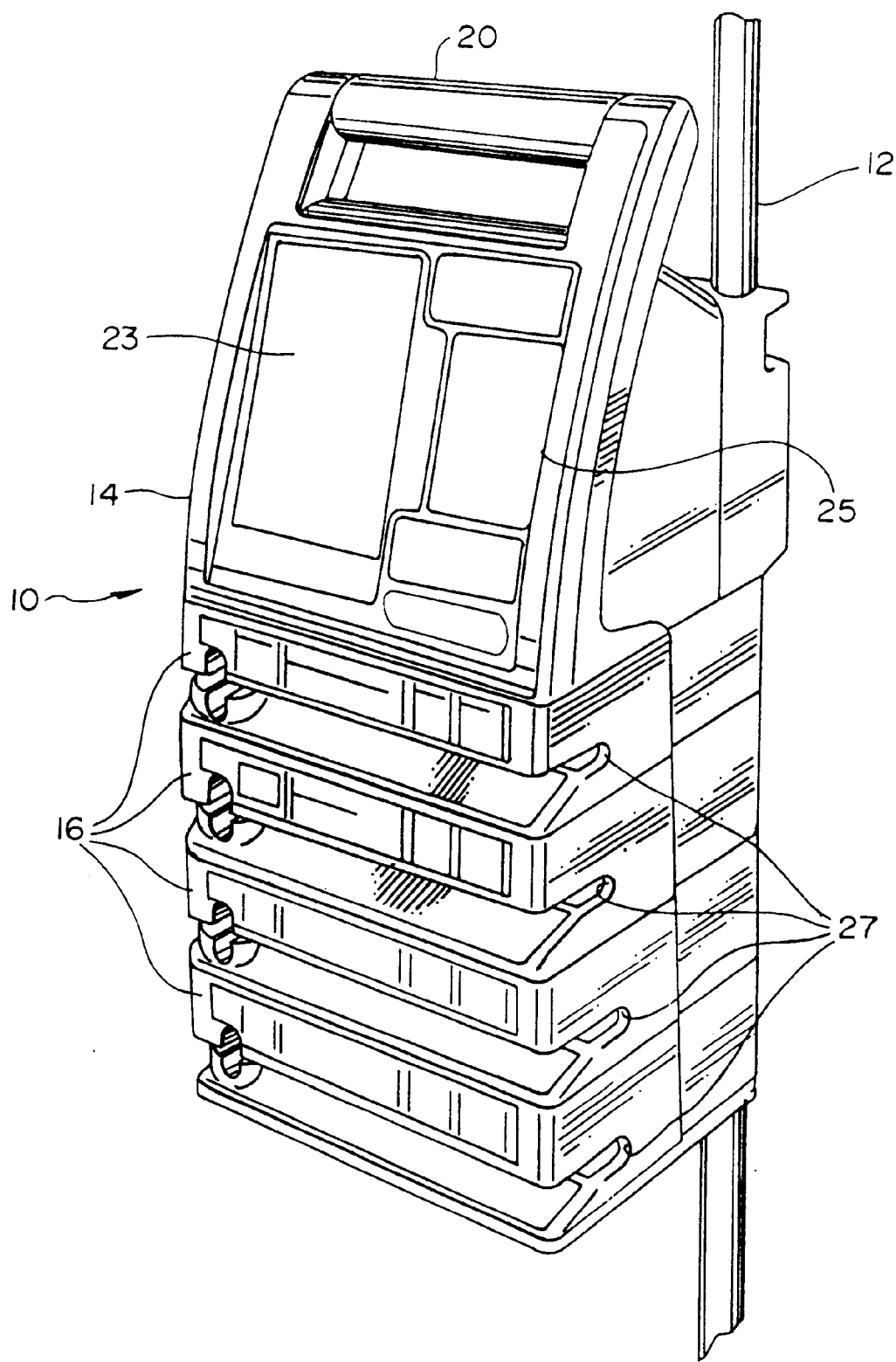
FIG. 2 is a perspective view of an alternative infusion pump.

Referring to FIG. 1, an intravenous fluid infusion pump is referred to generally as 10. The pump 10 is clamped onto a standard IV pole 12. The pump 10 includes a main body portion 14 and at least one pump module portion 16. In the embodiment depicted and described herein, two pump module portions 16 are provided. However, use of any number of pumping modules is contemplated depending on the requirements of the pump user. For example, FIG. 2 shows an infusion pump having four pumping modules 16.

Formed at the upper periphery of the main body portion 14 is a carrying handle 20. The main body 14 further includes a liquid crystal display (LCD) area 23 which is used to convey various information about the pump 10 to the user and provide for user interface with the pump 10, as described in more detail below. The main body 14 includes data-entry keys 25. The pump module 16 includes a tube-loading channel 27 and a display area 29 with a microprocessor. In a preferred embodiment, this microprocessor is a 68HC11 available from Motorola, Schaumburg, Ill. The main body portion 14 includes a slave microprocessor which is a slave to a master microprocessor. The slave microprocessor further includes an analog-to-digital converter (A/D converter). In a preferred embodiment, the master microprocessor is a 80C186EB available from Intel Corporation, Santa Clara, Calif. and the slave microprocessor is a 80C552 available from Philips Semiconductors, Sunnyvale, Calif. The slave microprocessor includes software in read-only memory (ROM), which drives the monitoring functions described below.

Figure 3:
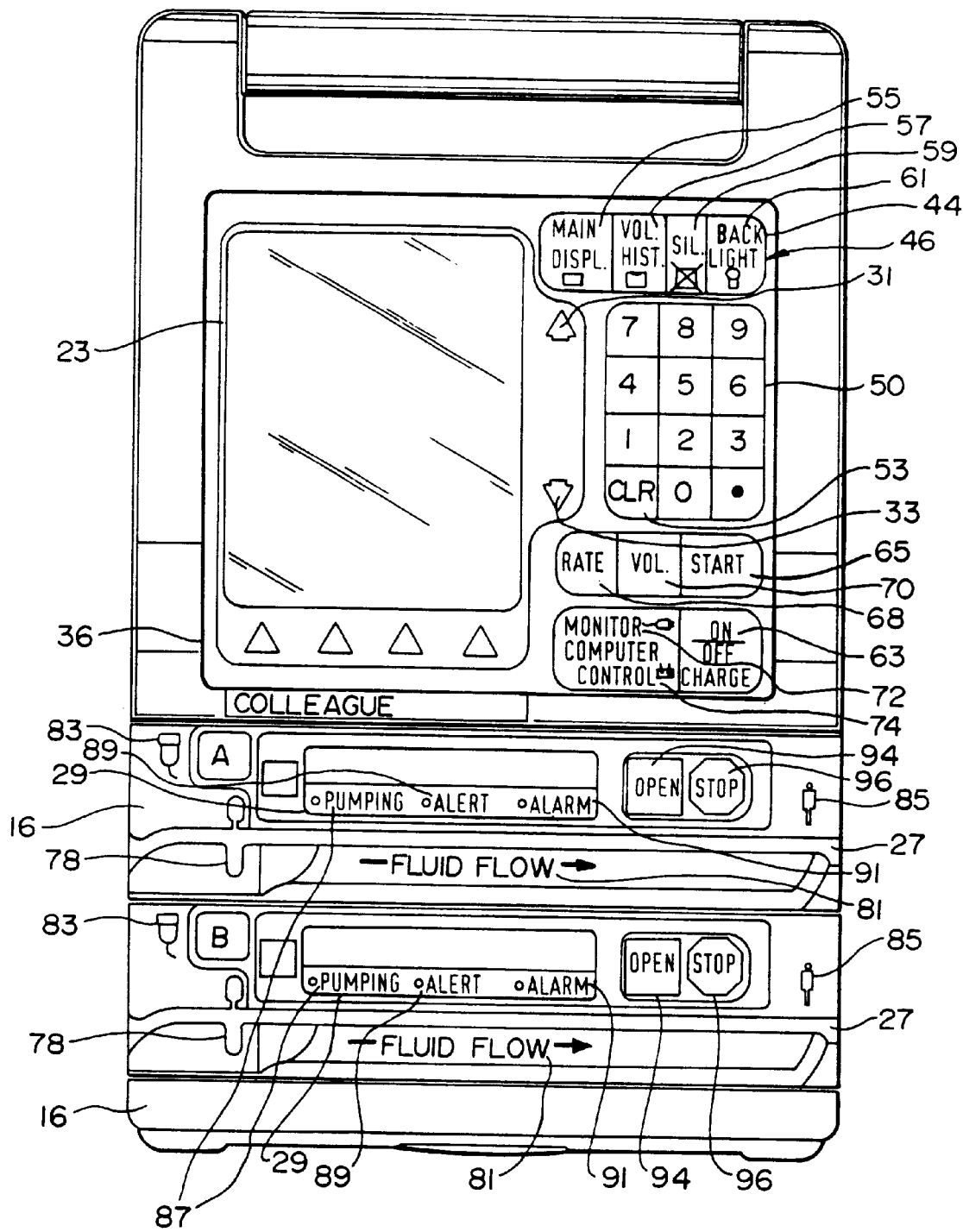
FIG. 3 is an elevational view of the infusion pump of FIG. 1, showing the detail of the pump face.

Referring to FIG. 3, an elevational view showing the detail of the face of the infusion pump 10 is seen. Contained along the side of the display area 23 are a scroll-up arrow key 31 and a scroll-down arrow key 33. These keys are used to select programming fields or actions within the display area. Contained beneath the display area 23 are a plurality of arrow keys 36 which are used to interact with selection alternatives in the display area 23. Because these arrow keys 36 are used in conjunction with the particular function displayed in the display area 23, these arrow keys 36 are referred to as "soft keys."

Figure 4:
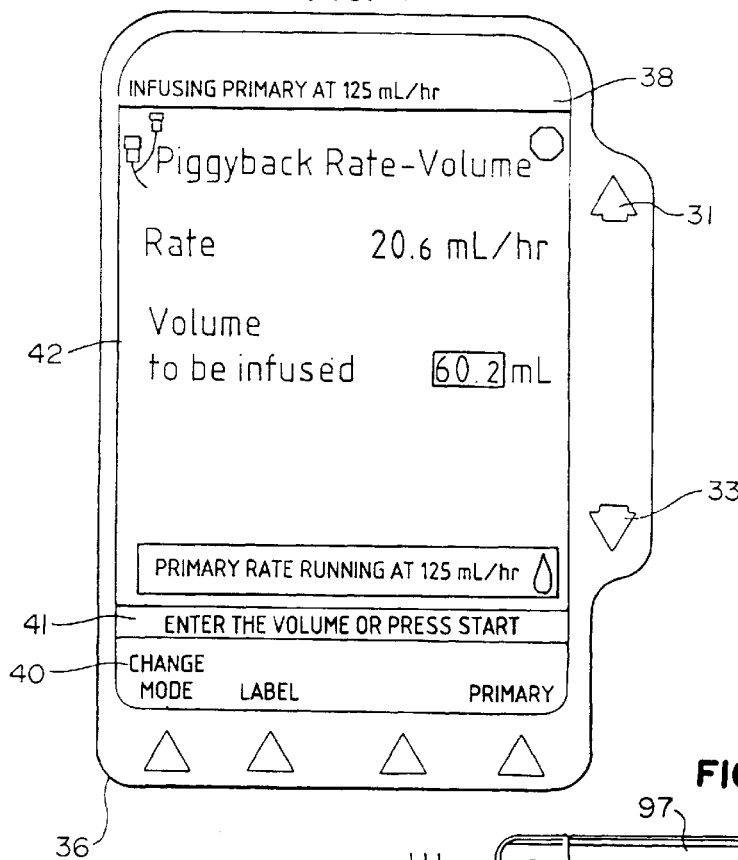
FIG. 4 is a detailed view of the display area of the infusion pumps of FIGS. 1 and 2.

Referring now to FIG. 4, the display area 23 includes four display portions. Located at the top portion of the display area is the status display 38. The status display 38 gives the status of the pump infusion. The status display 38 also identifies alert, alarm, and failure conditions. Contained at the lower portion of the display area 38 is the prompt display. The prompt display includes a prompt line 41 which provides prompts or instructions for the user. A soft key area 40 is further provided which contains labels for the plurality of soft keys 36 located beneath the display area 23. Thus, by following the prompts and making selections in accordance with the labels applied to the soft keys 36, the user can interface with the display screen. Finally, the middle portion 42 of the display area 23 is used for making infusion selections, programming, and displaying operating or running conditions of the pump infusion.

Referring back to FIG. 3, the main body 14 further includes a plurality of function keys 44. The function keys 44 include dedicated keys 46 which include user interface keys as well as a numeric key pad 50. Included in the numeric key pad 50 are the numbers zero through nine, and a decimal point key. These numeric and decimal point keys are used to enter programming values into the highlighted field in the display area 23, an example of which is seen in FIG. 4. The numeric key pad 50 further includes a clear key 53 which is used to clear values from the highlighted field. As a safety feature against inadvertent clearing of values from the highlighted field, if the clear key 53 is again pressed after the highlighted field has been cleared, the content of the field is restored to the last value stored in the master microprocessor.

The dedicated function keys 46 include a main-display function key 55. The main-display function key 55 is used to return the display area 23 to the initial or main display from any point in the user interaction. The volume-history function key 57 is used to display the volume history screen. The silence function key 59 silences pump alarms and pump alerts for a predetermined period, such as two minutes in the preferred embodiment. The back-light function key 61 serves one purpose when the pump is plugged into an electrical outlet, and a related but second purpose when the pump is on auxiliary battery power. When plugged into an electrical outlet, the back-light function key 61 turns the display back lights on and off. When on auxiliary battery power, the back-light function key 61 illuminates the display back lights, but in order to conserve power the back lights do not remain on after a preferred period of time.

Included in the action keys is an on/off charge key 63. The on/off charge key 63 powers the infusion pump 10 on and off. When the pump 10 is infusing, pressing the on/off charge key 63 will provide a system override to stop the infusion. The action keys further include a start key 65. If all of the required programming values have been entered during the programming mode, the start key 65 initiates the infusion. Following an alarm notification, once the alarm condition is resolved the start key 65 cancels the alarm notification and restarts the infusion. The action keys further include a rate key 68, which is used to select the rate values, and a volume key 70, which is used to select the volume parameters when the infusion pump 10 is programmed for an infusion.

Two additional icons are used as indicators of pump conditions. The electronic-plug icon 72 indicates when the infusion pump 10 is plugged into an electrical outlet. The electronic plug icon 72 also indicates that the auxiliary battery is being charged from the electrical power provided by the electrical outlet. A battery icon 74 is further provided, which is lit when the pump 10 is operating on auxiliary battery power.

At least one pump module 16 is located beneath the main body 14 of the pump 10. The pump module 16 include a tube-loading channel 27 into which a standard IV tube is loaded into the pump 10. The pump module 16 includes an automatic tube-loading feature. Contained within the tube-loading channel 27 is a keyed slot 78 adapted to receive a slide clamp 80 contained on the IV tube 76. The pump module 16 includes a free-flow prevention feature.

In order to assure that the IV tube is loaded into the pump module 16 in the proper orientation, the pump module 16 contains several safety features. Initially, the slide clamp 80 is keyed such that it only fits into the keyed slot 78 in the proper orientation. Additionally, beneath the tube-loading channel 27, a fluid flow arrow 81 is provided to instruct the user as to the proper direction of fluid flow in the IV tube. Still further, on the left side of the pump module 16 an intravenous solution bag icon 83 is provided. This reminds the user that the end of the IV tube that connects to the solution bag is to be directed to the left side of the tube-loading channel 27.

Still further, on the right side of the pump module 16 is a patient icon 85. This icon 85 is used to remind the user that the end of the IV tube that connects to the patient is to be directed to the right side of the tube-loading channel 27.

The pump module display area 29 further includes a character display area. In the embodiment depicted herein, an eight-character display area is provided. The display area is used to prompt or instruct the user during specific pump interaction operations. The display also is used during an alarm or alert condition to identify the particular condition. Finally, the display is used during infusion to provide an indication of status of the infusion.

Contained beneath the character display area are three light-emitting diode (LED) status indicators. The first is a green LED 87 which indicates when the pump is infusing. The second is a yellow LED 89 which indicates when the pump is in an alert condition. The yellow LED 89 remains continuously lit during an alert condition, provided there are no active alarms. The third is a red LED 91 which indicates when the pump is in an alarm condition. The red LED 91 flashes on and off during an alarm condition and remains lit continuously during a failure condition. If the infusion pump 10 is running on auxiliary battery power, the alert or alarm display will flash on and off in order to conserve battery power.

The pump module 16 also includes an open action key 94 and a stop-action key 96. The load/unload action key 94 opens the loading mechanism so that an IV tube can be loaded into the tube-loading channel 27. When an IV tube is contained in the pump module 16, the open action key 94 opens the loading mechanism to allow removal of the IV tube. The stop-action key 96 provides a system override to stop any active infusion.

Figure 5:
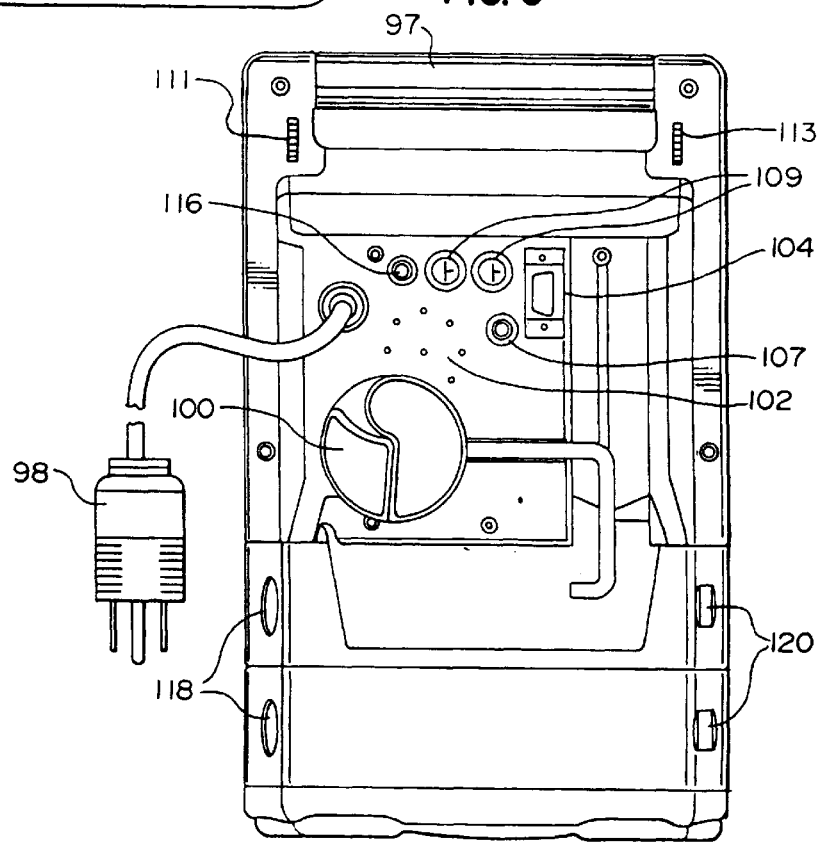
FIG. 5 is an elevational view of the rear of the infusion pump of FIG. 1.

Referring now to FIG. 5, the rear 97 of the infusion pump 10 is seen. The infusion pump 10 includes a grounded power cord 98 for plugging the pump 10 into a wall outlet to provide standard alternating current (AC) to power the infusion pump 10 and to recharge the auxiliary battery. The device further includes a mounting clamp 100 which is used to mount the ump 10 onto an IV pole. An audio speaker grill 102 is provided over an audio speaker which is used to generate alert and alarm condition audio tones. A communications port 104 is provided to allow the pump 10 to connect and communicate with a computer. The communications port 104 also can be used to communicate the nurse call signal to a computer located at a nurses station. In the preferred embodiment, an RS 232 compatible interface is provided for external communications.

A direct current (DC) receptacle 107 is further provided. The DC receptacle 107 enables the pump 10 to be connected to external DC power sources, such as for example, the 12-volt power source provided in most U.S. vehicles, to enable the pump 10 to be used with an ambulatory patient. The rear 97 of the infusion pump 10 further includes fuse compartments 109 which contain electronic fuses as known in the art, an audio speaker volume control 110, and an LED contrast adjustment 113 for the main display. Further provided is a panel lock button 116. Enabling the panel lock button 116 disables the front panel keys to prevent inadvertent reprogramming as well as deliberate tampering with the pump.

Contained on the side of each pump module 16 is a manual-tube release knob 118. This knob 118 provides a manual override of the automatic tube-loading and unloading feature in the pump module 16. This allows the user to manually release the tubing from the pump 10. Further provided on each pump module 16 is a drop-sensor port 120. This port 120 allows for connection to the pump 10 of an optional drop sensor, which is used in conjunction with a standard drip chamber.

Referring now to FIGS. 6 to 13, the user interaction with the infusion pump 10 is described. As previously discussed, the user interaction is principally conducted through the pump display area 23, including the scroll-up and scroll-down arrow keys 31, 33 contained on the side and the soft keys 36 displayed underneath the display area 23.

Upon power-up of the pump 10 by pressing the on/off charge key 63, the pump self-diagnostic tests begin. The main display area 23 initially is lit, then goes dark, while the pump module display 29 illuminates each of the character positions. Next, the LEDs are lit and the audible speaker is activated, followed by the sounding of the back-up buzzer. This procedure enables the user to check for dark spots or lines on the display when the screen is lit, check for light spots or lines on the display when the screen is dark, ensure that the pump module display characters are appropriately lit, ensure that all of the LEDs are in working order, and hear that the audible speaker and back-up buzzer tone are active.

Figure 6A:
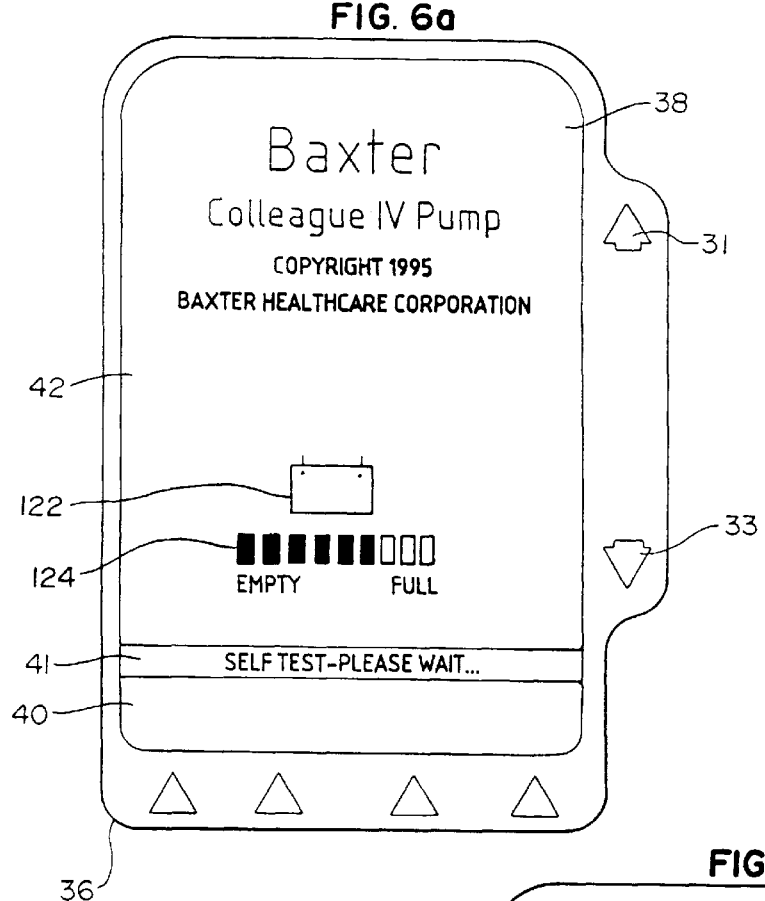
FIGS. 6 to 13 show the user interaction with the infusion pumps of FIGS. 1 and 2.

Once the display area, LED, and speaker tests are complete, the screen displays the pump identification screen seen in FIG. 6(a). This screen includes a battery icon 122. The battery, icon 122 includes a gauge 124 which graphically demonstrates the amount of amp hours remaining in the rechargeable auxiliary battery. In this initial screen, the prompt line 41 identifies that the pump self-diagnostic tests are proceeding and instructs the user to wait until the self-diagnostic tests are over.

Figure 6B:
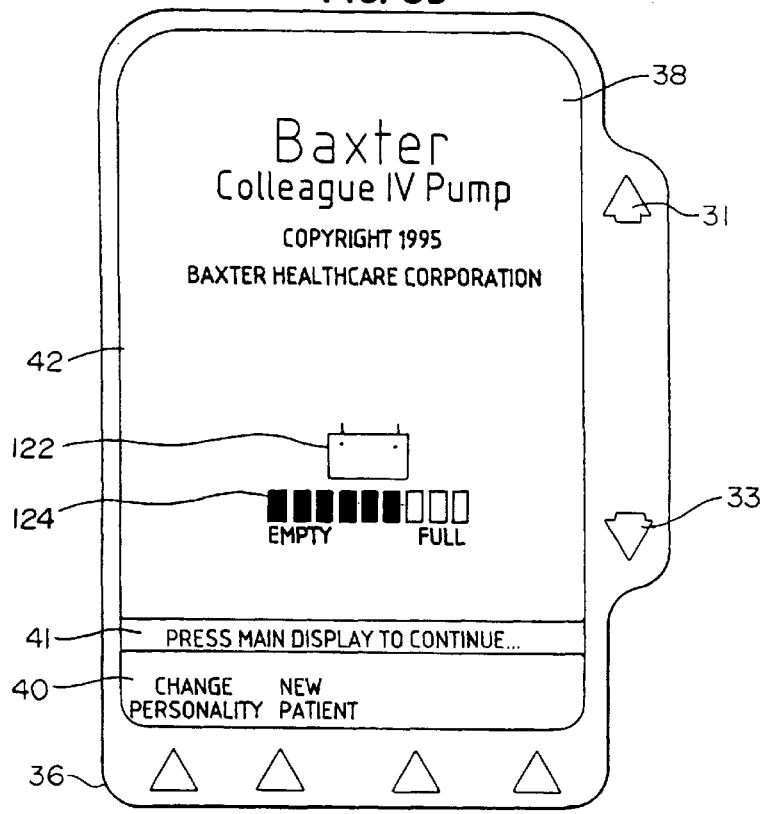
Figure 6C:
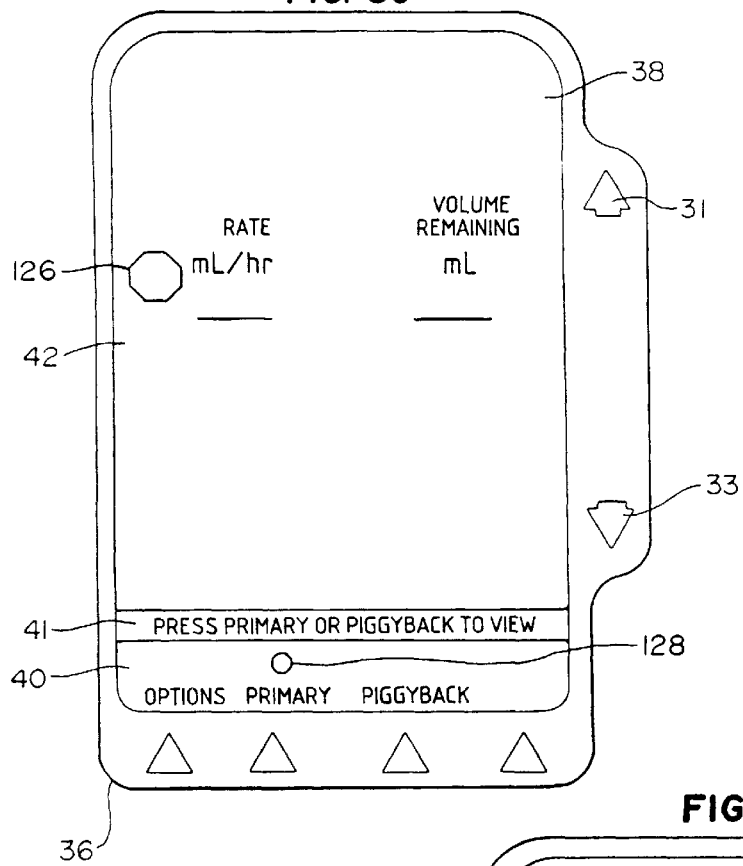

Referring now to FIG. 6(b), after the self-diagnostic tests are completed, the prompt line 41 instructs the user that the pump 10 is ready to continue into the programming mode. Additionally, several soft keys are made available depending on the configuration options chosen by the user. For example, in the embodiment depicted in FIG. 6(b), a soft key labeled "change Personality™" is present which enables the user to enter a programming mode to change the previously selected set of configuration parameters. Additionally, a soft key labeled "new patient" is present, indicating that information from a previous program is still retained in the memory. Pressing the "new patient" soft key will clear the programming memory and volume history from this previous patient. As instructed in the prompt line 41, pressing the main displays key 55 advances the display area to the main display screen.

Figure 7A:
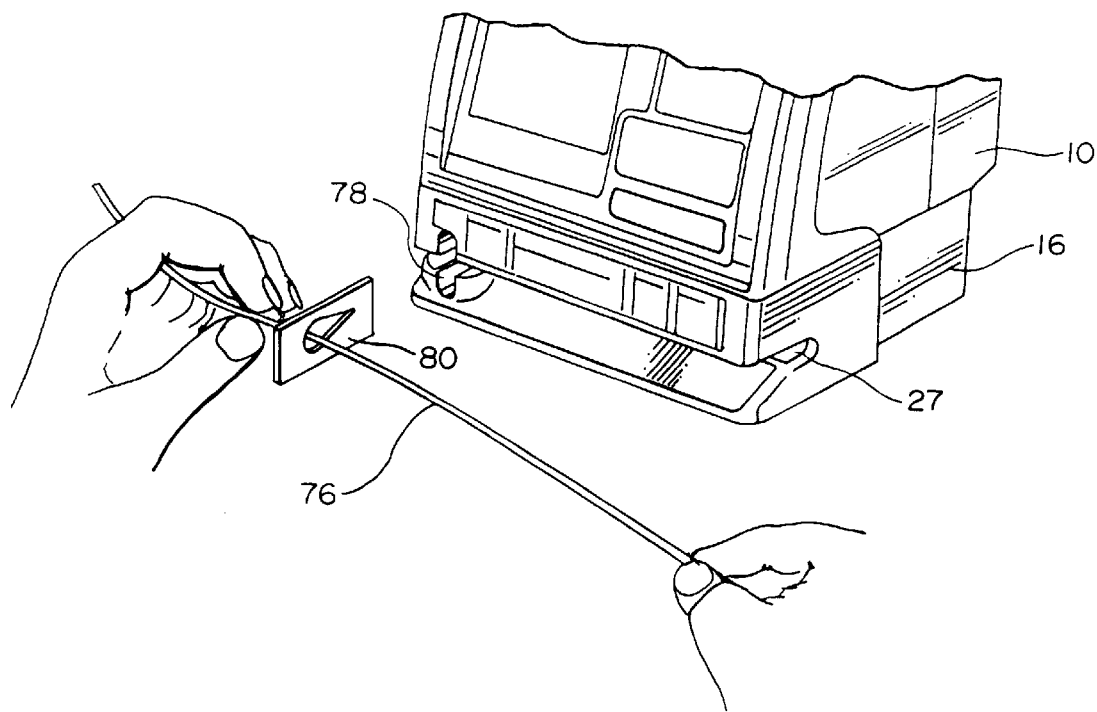
Figure 7B:
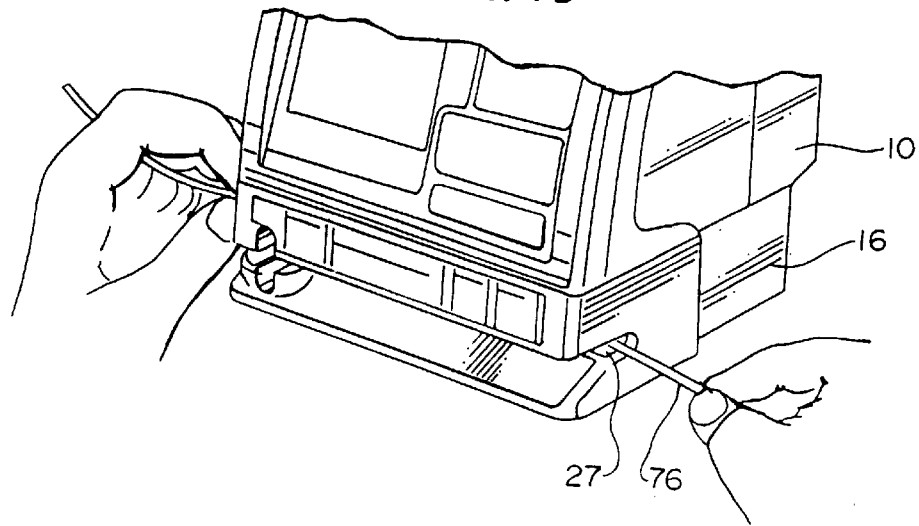

Prior to programming the infusion pump 10, the user is instructed to load an IV tube into the pump module 16. Referring now to FIG. 7, the loading of the IV tube into the automated tube-loading slot in the pump module 16 is described. Initially, the open key 94 is pressed, which causes the automatic tube-loading mechanism to open. As seen in FIG. 7(a), the user positions the on/off slide clamp 80 into the keyed slot 78, which helps assure the proper orientation of the IV tube. Pulling the IV tube taut, as seen in FIG. 7(b), the user slides the IV tube into and along the tube-loading channel 27. Once the pump 10 detects the presence of the IV tube, the pump 10 automatically loads the IV tube into the proper position in the pump drive mechanism. If the IV tube is not loaded in a given predetermined time period after the open key 94 has been pressed, the automatic tube-loading mechanism will close to assure that an inadvertent loading of an improper IV tube does not occur. Additionally, when off, pressing the open key 94 powers on the infusion pump 10 so that the IV tube can be loaded into the device.

The main display screen includes the stop icon 126 which indicates that the pump 10 is not infusing. The soft keys 36 include an "option" key, a "primary" key, and a "piggyback" key. A stop icon 128 contained above the "primary" soft key indicates the default infusion. The display screen prompt instructs the user to press the "primary" soft key or "piggyback" soft key to view the programming mode for those two infusions.

Figure 6D:
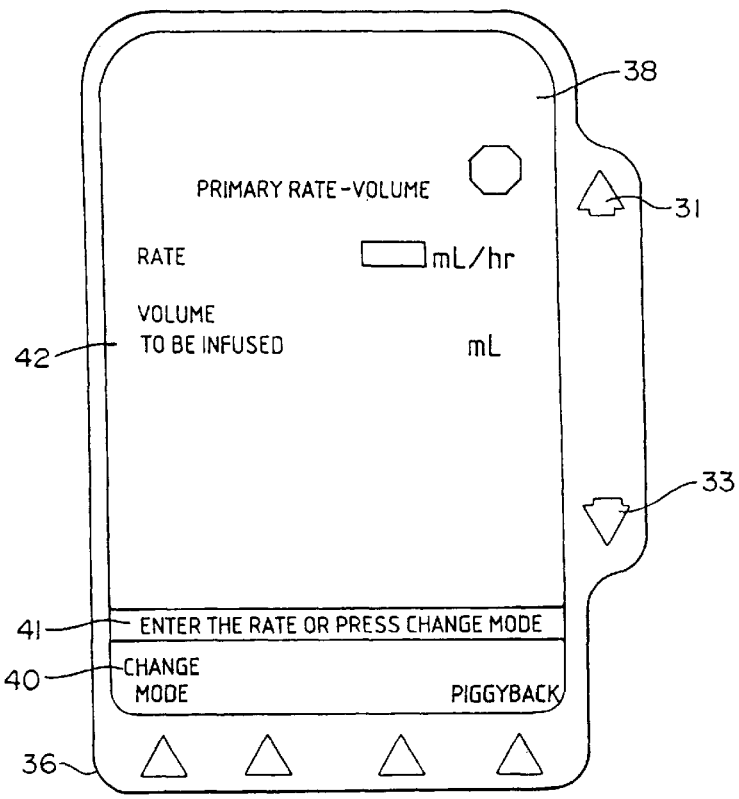

To begin programming the infusion pump 10, the rate key 68 is pressed, which changes the display to the rate-volume programming screen with the rate field highlighted, as seen in FIG. 6(d). If neither the "primary" soft key nor the "piggyback" soft key is pressed, the programming mode assumes the default infusion is to be programmed. The rate-volume programming screen prompt line instructs the user to enter the rate or press change mode while the soft key options include the "change mode" key and the "piggyback" key. Once the desired flow rate is entered by the user into the numeric key pad 50, either the volume or the arrow key can be used to highlight the volume field. The volume to be infused can then be entered by the user using the numeric key pad. For standard primary infusion, this completes the programming steps.

During programming, if incorrect values are entered by the user, pressing the clear key 53 clears the incorrect value so that the correct value can be programmed using the numeric key pad 50. To begin the infusion, the start key 65 is pressed. If the programmed values exceed an allowable range preprogrammed into the master microprocessor based on the particular set of configuration parameters chosen by the user, an out-of-range alarm will be activated upon pressing the start key 65.

When infusing, the display area will show as a droplet icon an animated drop of water to indicate that the pump is operational. The program rate of delivery, the volume of fluid remaining to be delivered, and/or the time remaining to deliver the remaining volume will be displayed. To stop an infusion before it is completed, the stop key 96 is pressed. The droplet icon will be replaced with the stop icon on the main display, and the pump LED will no longer be illuminated. To restart the infusion, the start key 65 is pressed.

If the pump 10 is not restarted within a predetermined period of time, a channel stop alert will sound. The pump 10 also can be stopped if any alarm condition occurs or if the on/off charge key 63 is pressed while running. A piggyback infusion is stopped by closing the slide clamp 80 on the secondary infusion IV tube and pressing the stop key 96. To continue with the primary infusion, the "primary" soft key is pressed to change the operation mode of the pump 10, followed by the pressing of the start key 65 to begin the primary infusion.

Once the volume remaining to be infused reaches zero, indicating the infusion is concluded, the pump 10 will automatically enter a keep-vein-open (KVO) alert mode. During this alert mode, the pump 10 will continue infusing at the lesser of a preprogrammed KVO rate or at the programmed rate. To exit the KVO alert mode, the stop key 96 is pressed. The pump 10 can then be programmed for the next infusion or the pump 10 can be powered off.

After the end of the infusion, to unload the IV tube, the open key 94 is pressed. The pump module 16 automatically closes the slide clamp 80 and opens the tube-loading channel 27 to allow removal of the IV tube. Upon removal of the IV tube, the auto load mechanism will close. Alternatively, if the IV tube has not been removed after a predetermined time period, the mechanism will automatically close.

Figure 8:
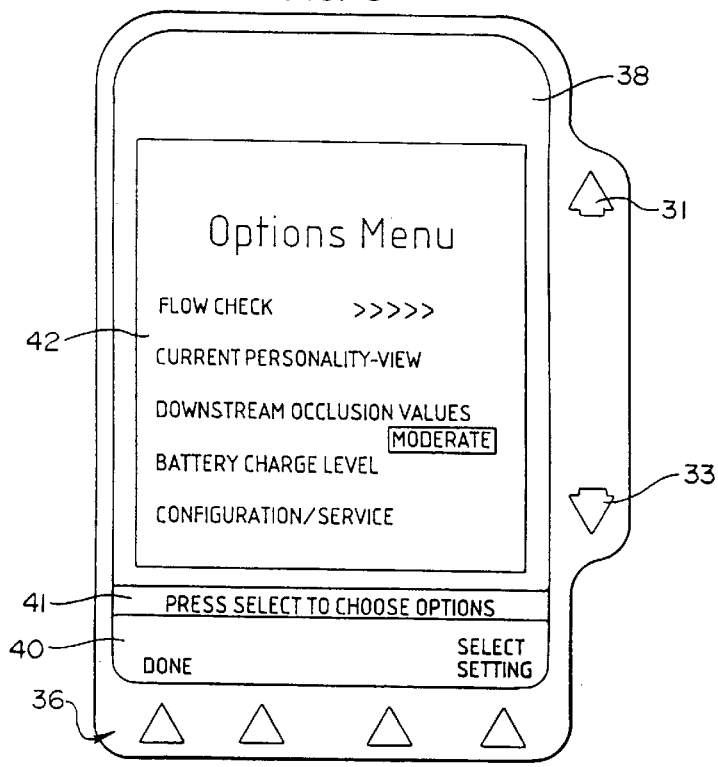

Referring now to FIG. 8, a pop-up window is seen which displays an options window if the "options" soft key is pressed from the main menu. The options display includes a flow check feature, a current Personality™ view feature, a selection of the downstream occlusion values, the battery charge level feature, and the configuration/service feature. In order to view particular available features, the user highlights the feature to be viewed using the scroll-up and scroll-down arrow keys 31, 33. The current Personality™ view feature allows a quick review of the current set of configuration parameters.

Figure 9:
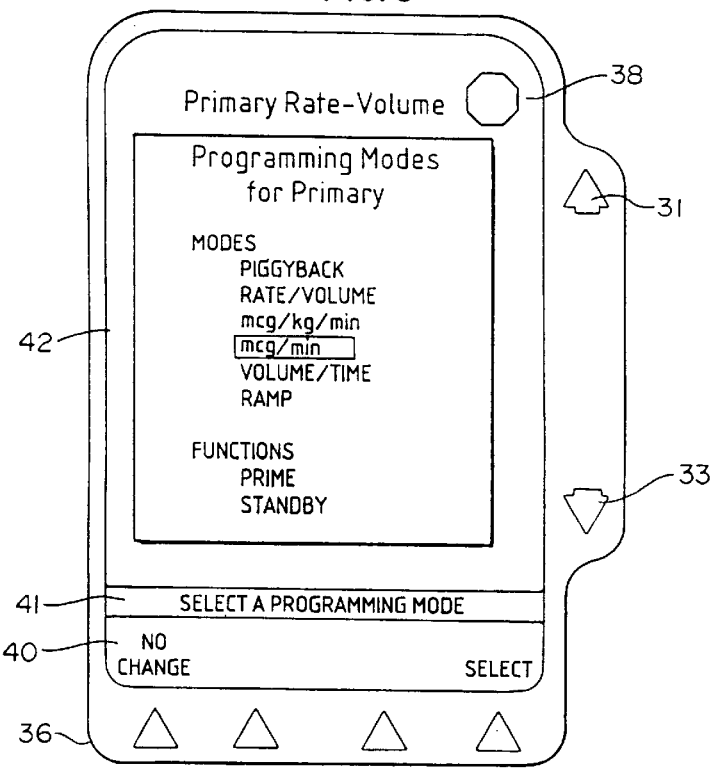

The present invention also provides several available programming modes for primary infusion. Upon selection of the "change mode" soft key in the programming mode display, if the programming mode is in the primary programming function, an options window as seen in FIG. 9 is displayed. The options window includes mode and function subsets. The function subset includes a prime function.

Figure 10A:
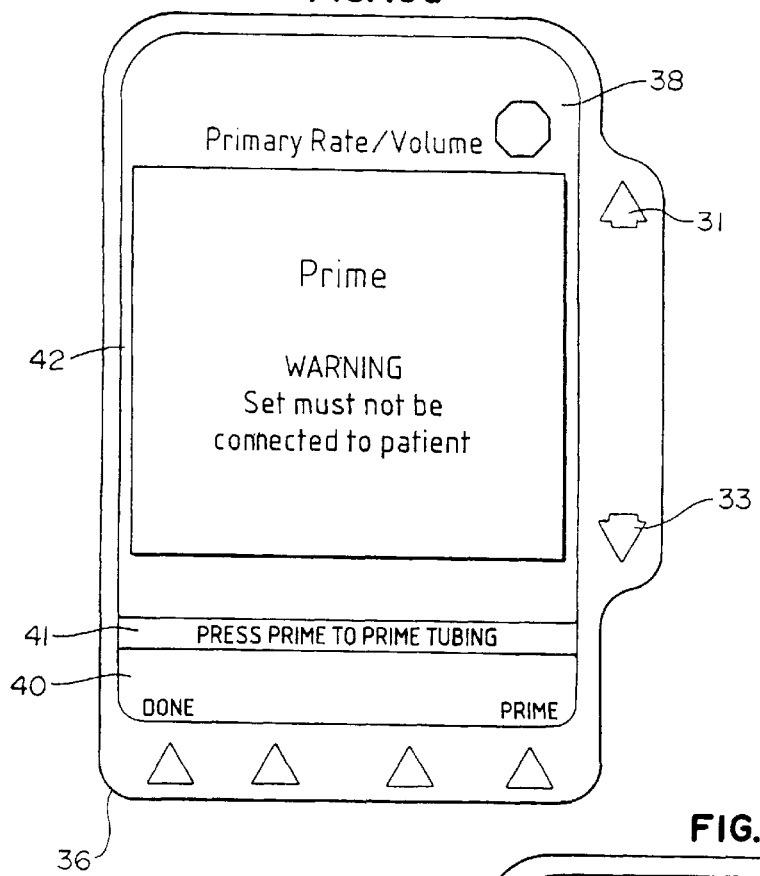
Figure 10B:
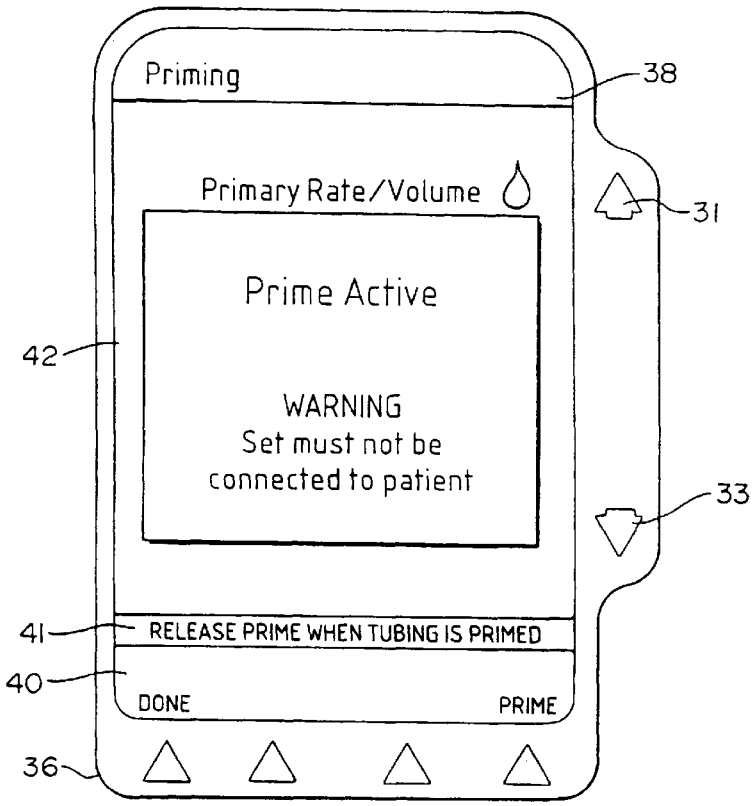

The prime function is used to assist users in priming the IV tube in order to ensure that no air is in the IV tube prior to infusion. In the primary programming mode, after the IV tube has been loaded, the prime function is accessed by pressing the "change mode" soft key. The scroll-up and scroll-down arrow keys 31, 33 can be employed to highlight the prime field, which can be selected by pressing the "select" soft key. The display area then displays the prime message window, as seen in FIG. 10(a). The prompt line 41 instructs the user to press the "prime" soft key to prime the IV tube. A "done" soft key also is provided to indicate when the prime function has been completed. While priming is active, the display area shows the prime message window seen in FIG. 10(b). Pressing the "done" soft key upon completion of priming returns the display area to the primary infusion program.

The present invention also provides several troubleshooting alert, alarm and failure messages. When an alert, alarm or failure message occurs, the status area of the display, as well as the pump module character display, identifies the alert, alarm or failure. Alert messages may require a user intervention, but do not stop the infusion. Alarm conditions automatically stop the infusion and require immediate attention before infusion can be restarted. A device failure automatically stops any infusion. An alarm condition overrides an existing alert condition while a failure overrides all alerts and alarms.

Figure 11A:
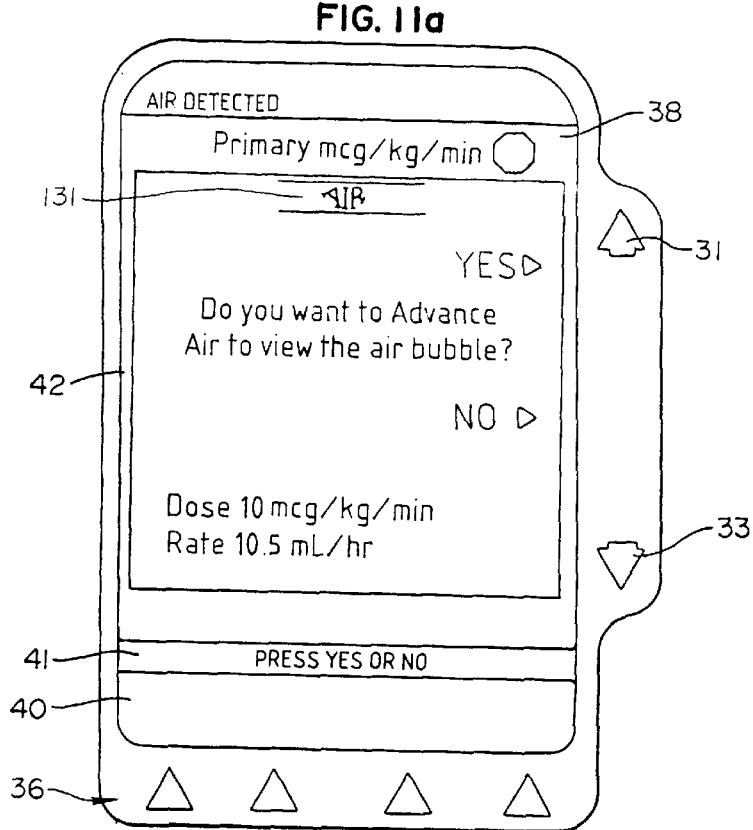
Figure 11B:
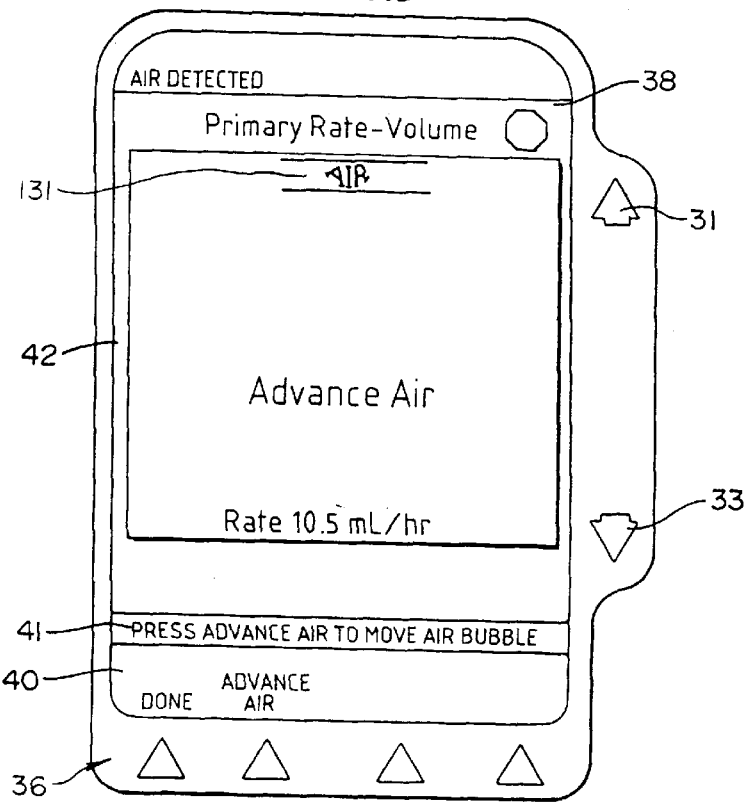
Figure 11C:
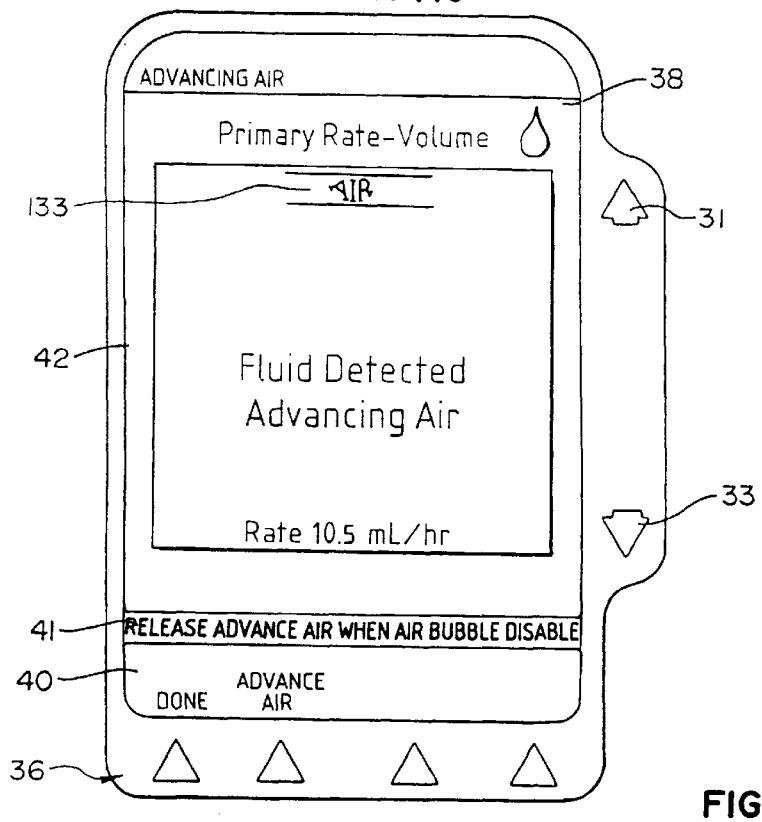
Figure 11D:
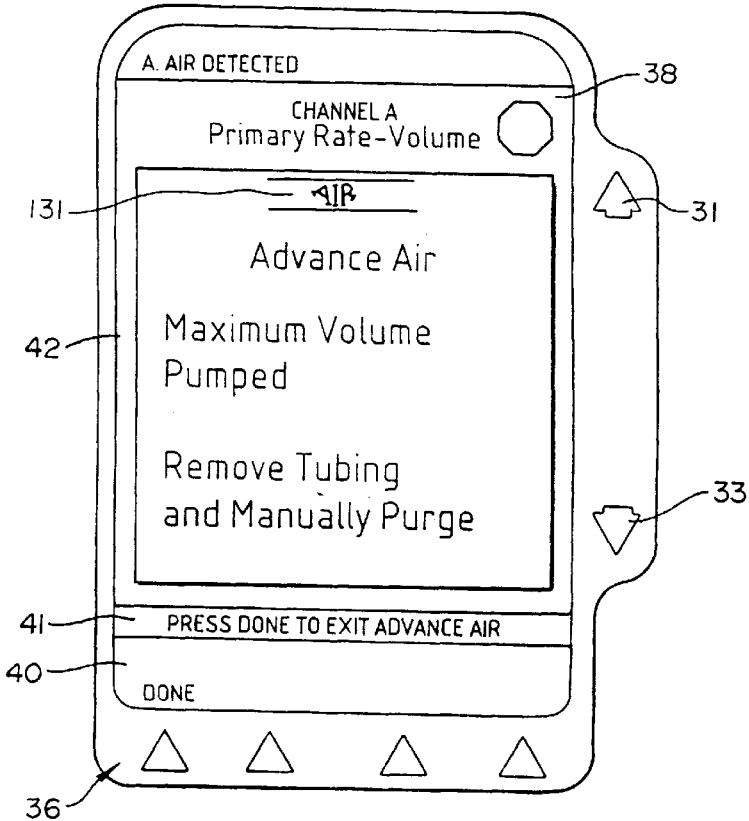

An alert condition lights the yellow alert LED 89 beneath the pump module display 29, and sounds the alert tone. The alert tone can be silenced for a period of time, such as two minutes, by pressing the silence key 59. The alert conditions include advanced air alert, which indicates that a detected air bubble is in the IV tube, as described in detail below. As seen in FIG. 11(a), the display area displays the air-in-line icon 131 and asks the user if the advance air feature is desired to be used to view the air bubble. Choosing the advance air feature advances the display screen to the "advance air" screen depicted in FIG. 11(b). To advance the air bubble, the user presses and holds the "advance air" soft key. When the air detect feature again detects liquid, the display area will inform the user of the liquid detection by displaying the liquid icon 133, seen in FIG. 11(c). The user can continue to advance the air bubble until a predefined limit is reached. Upon sensing liquid at the air sensor location and the appearance of the liquid icon 133, the alarm condition can be reset and the infusion can be restarted by pressing the start key 65. A user can advance air until a maximum defined volume has been pumped. Once this maximum volume has been pumped, the display informs the clinical user, as seen in FIG. 11 (d)e. The IV tube should be removed and manually purged to reset the alarm.

To configure the set of configuration parameters for the pump, the configuration/service function of the options menu seen in FIG. 8 is selected. Upon selection of the configuration/service function, a password entry screen seen in FIG. 12(a) appears. The password ensures that only proper hospital personnel access the configuration/service routine. The prompt line 41 directs entry of the password. The authorized personnel enters a numeral password in order to proceed in the configuration/service routine. The password entry screen includes a reference listing of the software versions in the infusion pump. A "cancel" soft key is provided to exit the routine.

Figure 12A:
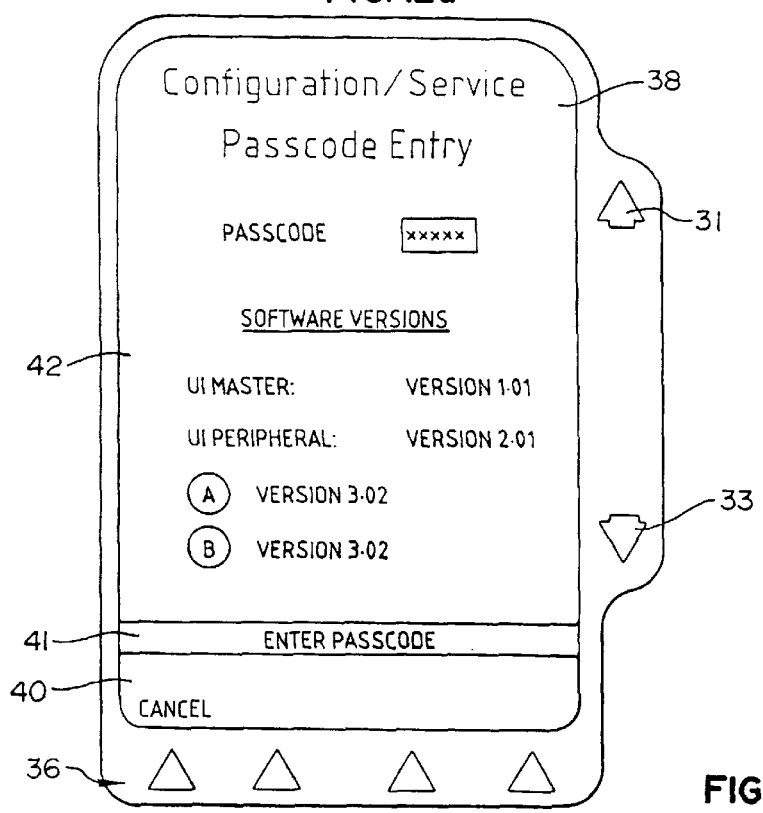
Figure 12B:
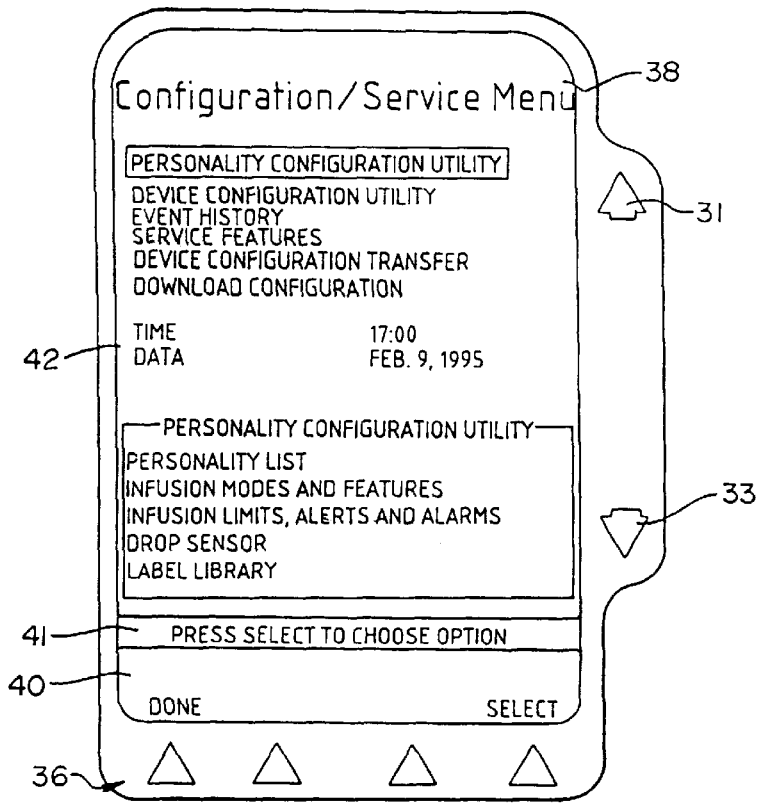
Figure 12C:
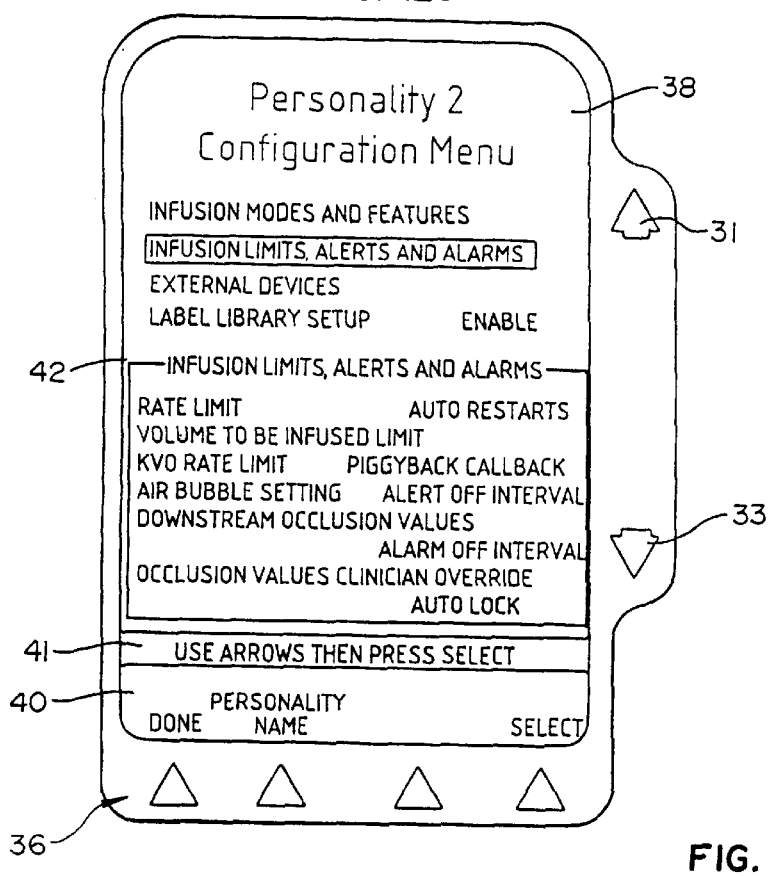

Upon successful entry of a valid password, a configuration/service menu screen as seen in FIG. 12(b) appears. The options include Personality™ configuration utility, device configuration utility, event history, service features, device configuration transfer, download configuration, time set and date set. When an option is highlighted, a message appears giving the particular components of an option. In the example seen in FIG. 12(b), the Personality™ configuration utility includes as components a Personal list, infusion modes and features, infusion limit alerts and alarms, drop sensors, and label library.

Figure 12D:
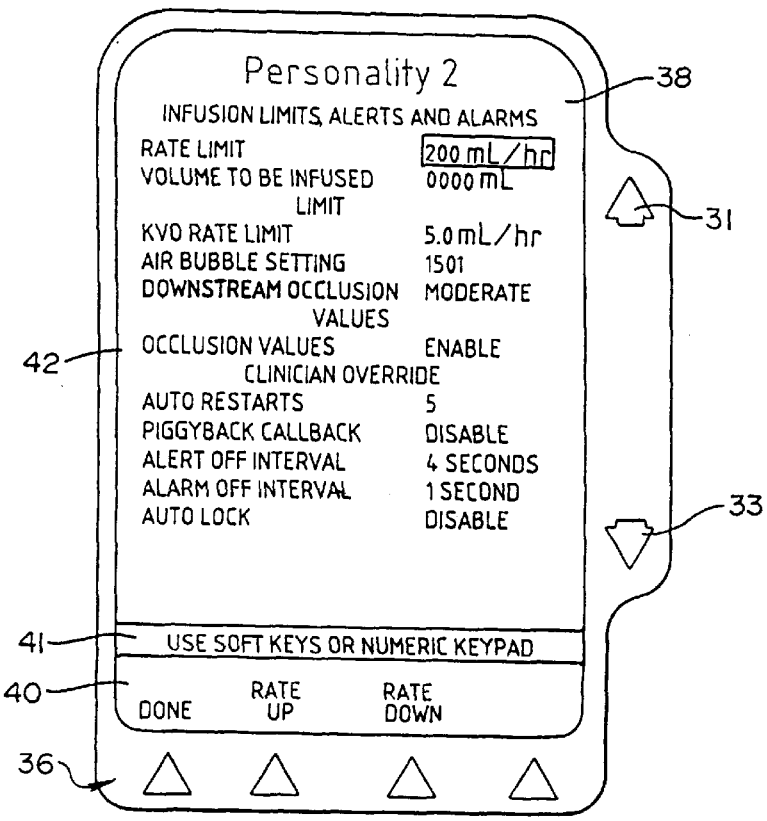

Authorized hospital personnel can program clinical feature limits and infusion alert and alarm characteristics. The infusion limits, alerts and alarms are accessed from the Personality™ configuration menu, seen in FIG. 12(c). Upon selection, the infusion limits, alerts and alarms menu seen in FIG. 12(d) is displayed. The settings in this menu apply to the infusion pump 10 as a whole and are not programmable for separate channels.

Figure 13:
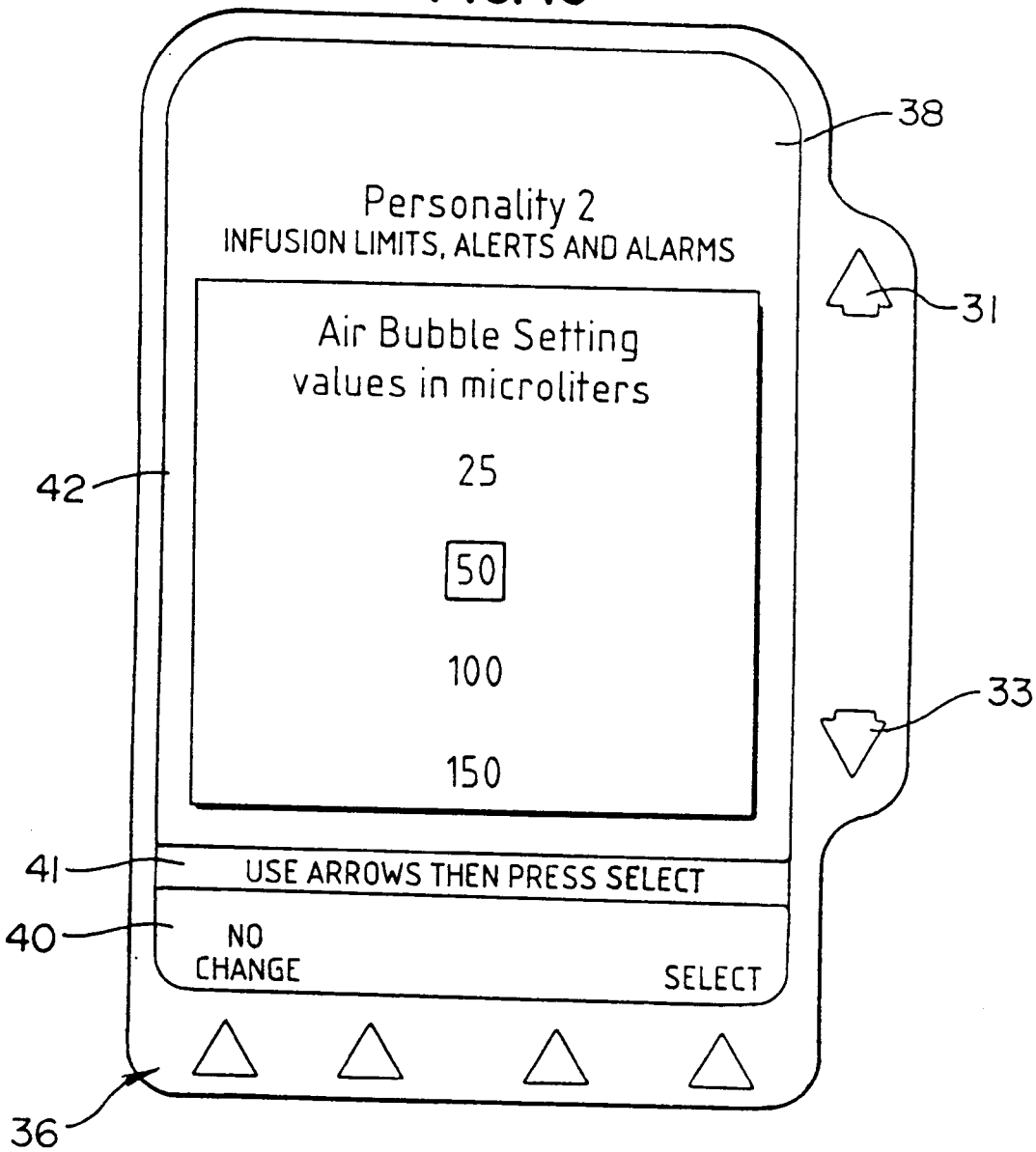

The authorized hospital personnel can set the size of the air bubble to be detected by the infusion pump 10. Referring to FIG. 13, an air bubble select pop-up window which is displayed upon selection of the air bubble setting is seen. The screen includes a "no change" soft key and a "select" soft key. Options on the bubble size are displayed. In a preferred embodiment, four bubble size levels are expressed. In the preferred embodiment described herein, the four bubble size levels are 25 microL, 50 microL, 100 microL and 150 microL. Each bubble size level will detect air bubbles within a given range. For example, the 25 microL level will detect air bubbles above 25 microL and will not detect air bubbles below 10 microL; the 50 microL level will detect air bubbles above 50 microL and will not detect air bubbles below 25 microL; the 100 microL level will detect air bubbles above 100 microL and will not detect air bubbles below 50 microL; and the 150 microL level will detect air bubbles above 150 microL and will not detect air bubbles below 100 microL.

Figure 14:
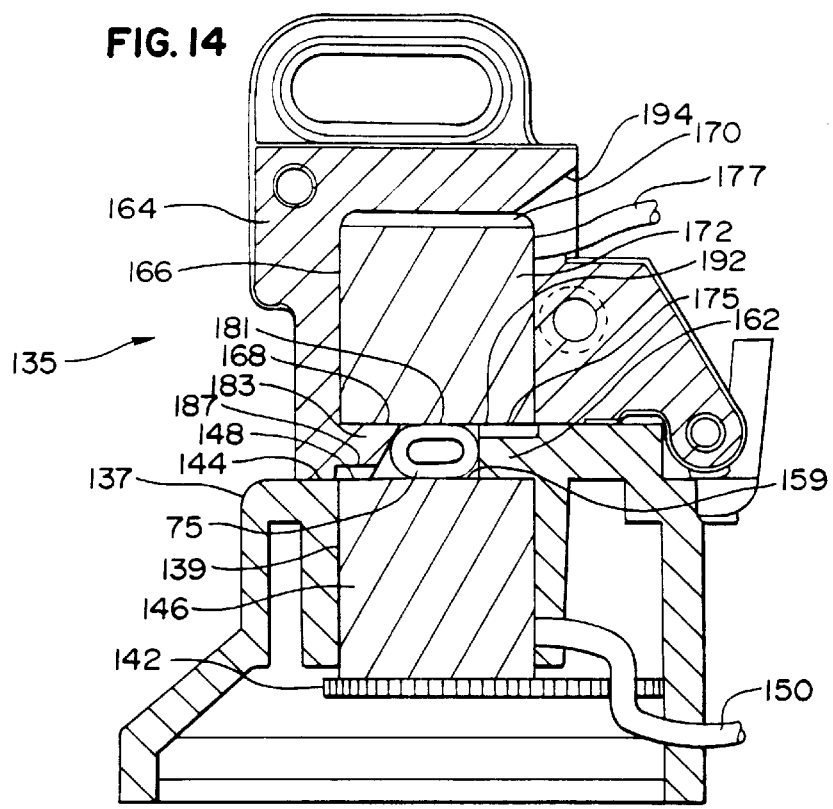
FIG. 14 shows the detail of an air sensor constructed in accordance with the principles of the present invention.

Referring now to FIG. 14, the air sensor 135 is seen in detail. Located in the transmitter housing 137 is the transmitter can 139. The transmitter can 139 rests on a retaining plate 142, which biases the transmitter can 139 upwardly against a transmitter platum face 144. The transmitter can 139 includes an ultrasonic crystal 146 encased in stycast epoxy. Contained below the ultrasonic crystal 146 is a copper disk 148 which is approximately the diameter of the ultrasonic crystal 146. The copper disk 148 acts as an electrical barrier against ambient noise such as for example interference from electrosurgical units. A coaxial cable 150 is provided to electrically connect the ultrasonic sensor to a transmitter circuit, as described in detail below. The outer sheath of the coaxial cable 150 is grounded first to the copper disk 148, then to the front face of the ultrasonic crystal 146 closest to the IV tube. The center conductor of the coaxial cable 150 is threaded through a hole in the copper disk 148 to the back face of the ultrasonic crystal 146 furthest from the IV tube. This configuration also helps shield against outside interference. The transmitter housing 137 defines a tube rest area 159 in which the transmitter can 139 and the transmitter housing 137 are flush to define a flat area. The tube rest area 159 includes an upwardly extending rear wall 162 against which the IV tube 76 is registered when it is loaded. The tube rest area 159 is unobstructed so that no alternate path for the ultrasonic signal is present and a clear ultrasonic signal can be transmitted directly through the center of the tube.

Located in the receiver housing 164 is the receiver can 166. The receiver can 166 is located within the receiver housing 164. The receiver can 166 is biased downward against a receiver platum face 168 by a retaining plate 170. The receiver can 166 includes an ultrasonic crystal 172 encased in stycast epoxy. Contained above the ultrasonic crystal 172 is a copper disk 175. A coaxial cable 177 is provided to electrically connect the ultrasonic sensor to a receiver circuit, as described in detail below. The outer sheath of the coaxial cable 177 is grounded first to the copper disk 175, then to the ultrasonic crystal 172. The center conductor of the coaxial cable 177 is threaded through a hole in the copper disk 175 to the ultrasonic crystal 172. This configuration helps shield against outside interference.

The receiver housing 164 defines a tube-secure area 181 in which the receiver can 166 is flush with the receiver housing 164 to define a flat area. The tube-secure area 181 includes a downwardly extending step 183, which extends downwardly opposite the upwardly extending rear wall 162. The tube-secure area 181 is unobstructed so that no alternative acoustic path for the ultrasonic signal is present and a clear ultrasonic signal can be received. The tube rest area 159, tube-secure area 181, the upwardly extending rear wall 162, and the downwardly extending step 183 act to secure the tube 76 in the proper position between the transmitter can 139 and the receiver can 166.

To further ensure that no alternative acoustic path is provided between the transmitter can 139 and the receiver can 166, the transmitter housing 137 defines an air-insulating area which, when the IV tube 76 is secured, provides an air gap 187 between the receiver 164 and the transmitter housing 137. Likewise, the receiver housing 164 defines an air-insulating area which, when the IV tube 76 is secured, provides an air gap 192 between the transmitter 137 and the receiver housing 164.

The IV tube 76 is contained between the transmitter can 139 and the receiver can 166. The IV tube 76 is secured in proper position by the upwardly extending rear wall 162 of the transmitter housing 137 and the downwardly extending step 183 of the receiver housing 164. The air gap 192 provided by the air-insulating area of the receiver housing 164 and the air gap 187 provided by the air-insulating area of the transmitter housing 137 eliminate alternative acoustic paths between the transmitter can 139 and the receiver can 166, so the only path for the ultrasonic signal is through the IV tube 76. The coaxial cable 177 which electrically connects the receiver can 166 to the receiver circuit extends through a wide-angle aperture 194 defined in the receiver housing 164 to enable movement of the receiver housing 164 so the IV tube 76 can be inserted into position.

Figure 15:
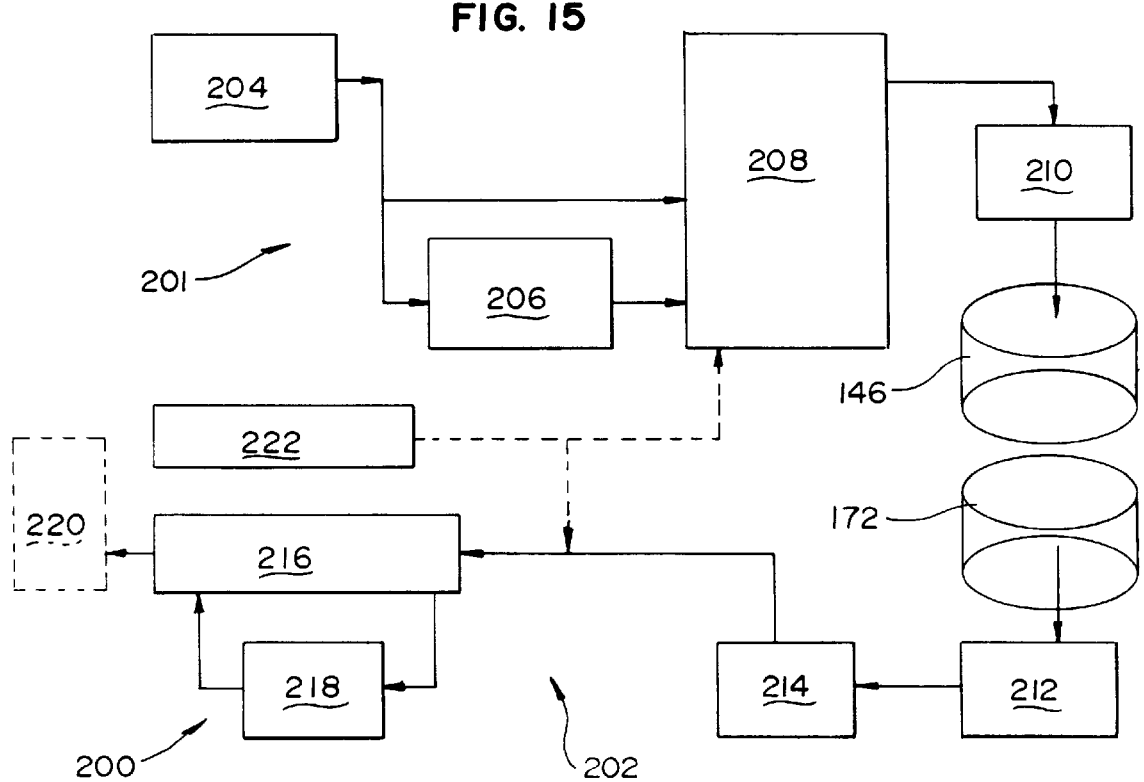
FIG. 15 is a block diagram of an air detector circuit constructed in accordance with the principles of the present invention.

Referring now to FIG. 15, a first embodiment of a circuit 200 for the air sensor is seen in block diagram. The circuit includes both a transmitter circuit 201 and a receiver circuit 202. The transmitter circuit 201 includes means for generating an oscillation 204 which, in a preferred embodiment, is a 4.5 MHz oscillator. The oscillator 204 provides the primary signal to the air sensor transmitter. In order to provide a test to detect variations in the receiver gain and to check the level of interference, a second signal is provided by a test means 206 for adding an attenuation to the primary signal to derive a test signal. In the preferred embodiment, the signal amplitude is reduced by approximately 15 db. On power-up, a test mode is used which utilizes the test signal. During the test mode, the value received by the receiver circuit is checked to ensure a corresponding reduction. In a further preferred embodiment, the test mode can be used intermittently.

The primary signal and the test signal are input into means for switching 208 which, in the preferred embodiment, is an analog gate switch. The switching means 208 selects one of the two signals to be provided to an ultrasonic transmitter 146. After a gain 210 is provided to the selected signal, the signal is applied to the ultrasonic transmitter 146.

The receiver circuit 202 includes an ultrasonic receiver 172 which is positioned to receive the ultrasonic signals transmitted from the ultrasonic transmitter 146. After a gain 212 is applied by a preamp, which in a preferred embodiment is approximately 13 db, the primary signal is applied to a receiver/demodulator 216 through a filter 214 which, in a preferred embodiment, is a 4.5 MHz bandpass ceramic filter. In a preferred embodiment, the superheterodyne receiver/demodulator is a Signetics SA 637 available from Signetics Corporation, Sunnyvale, Calif. The receiver/demodulator 216 further filters 218 the signal to provide extreme rejection of unwanted spurious signals and converts the signal from the ultrasonic receiver into a calibrated output direct current. In a preferred embodiment, the second and third filters are PBFS450P-30K 450 KHz bandpass ceramic filters available from AVX/Kyocera Corporation, Myrtle Beach, S.C. This signal is then conditioned and input into an A/D converter 220, which provides a digital signal representative of the radio frequency signal received at the ultrasonic receiver. A control circuit 222 further is provided to provide control to the transmitter circuit 201 and the receiver circuit 202.

Figure 16A:
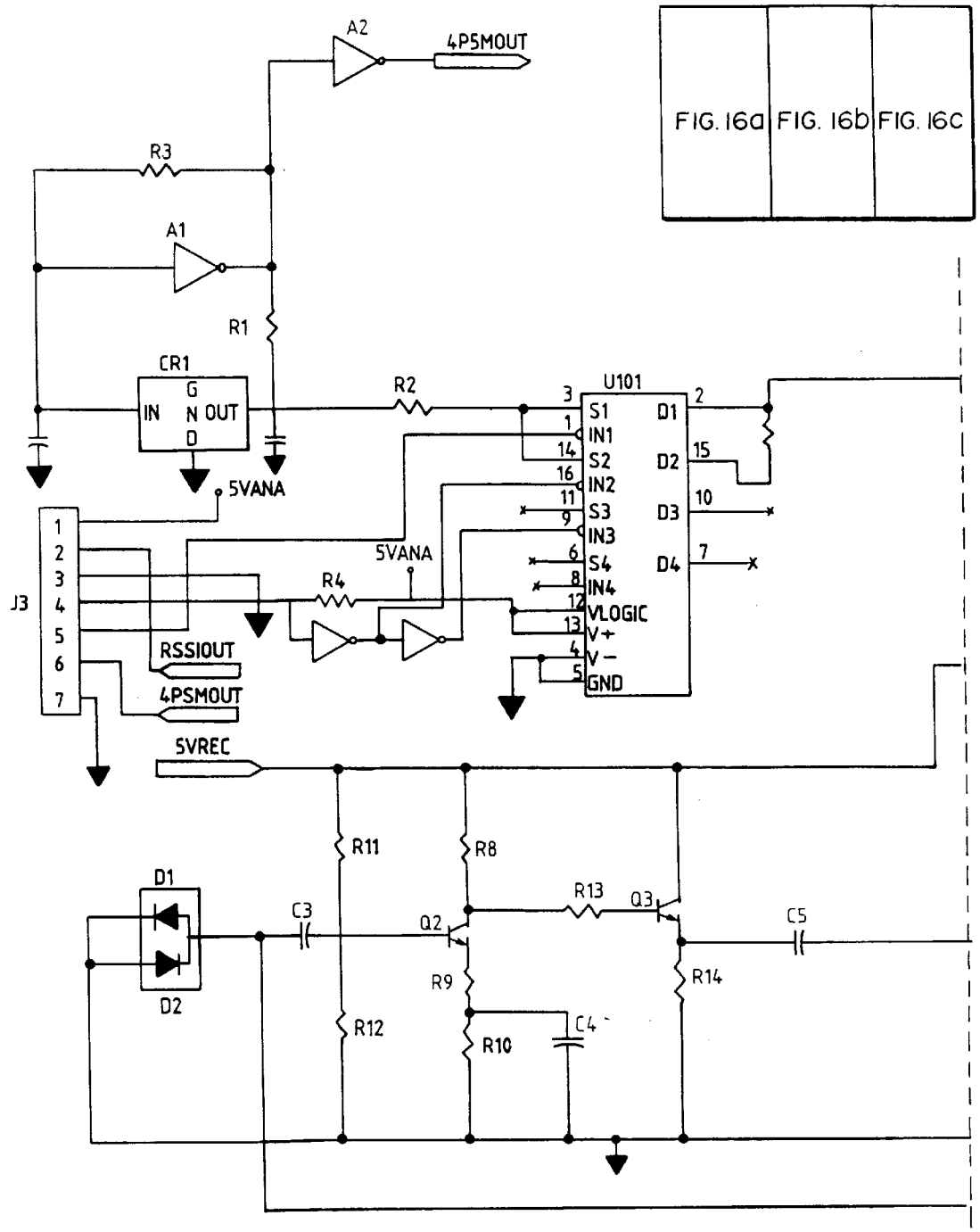
FIG. 16 is a schematic diagram of an air detector circuit constructed in accordance with the principles of the present invention.
Figure 16B:
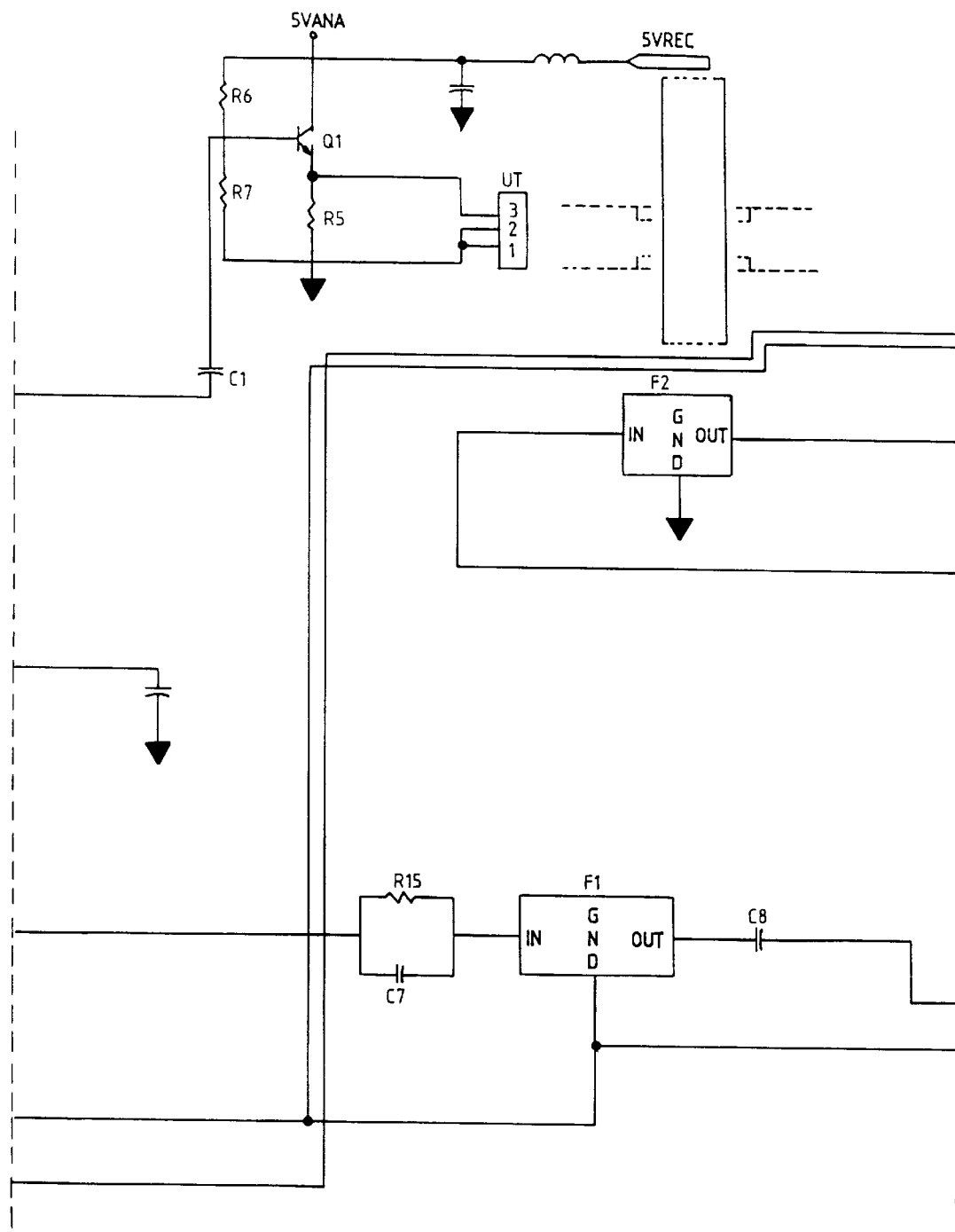
Figure 16C:
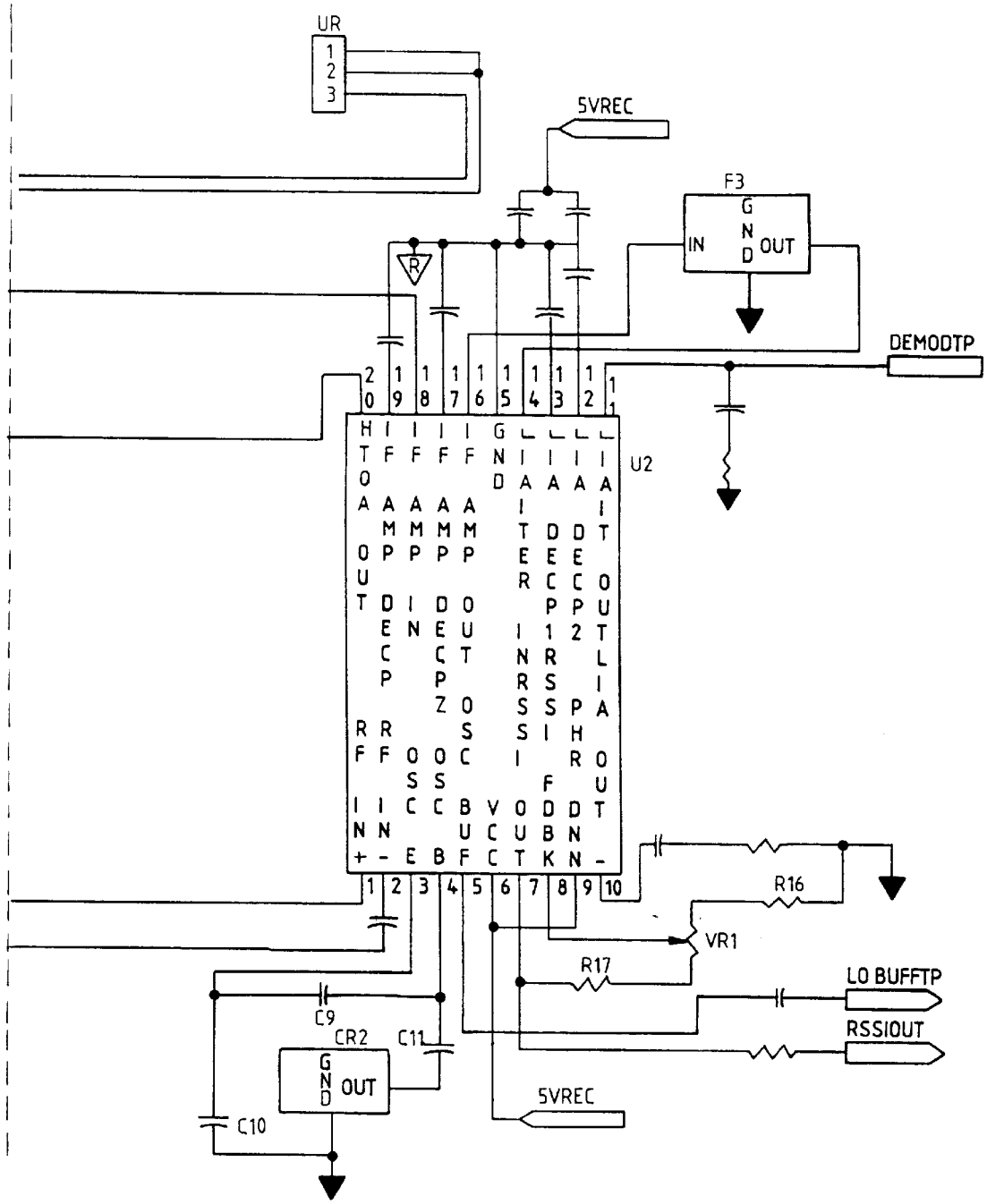

Referring now to FIG. 16, a schematic of the first embodiment of the circuit for the air sensor is seen. Referring first to the transmitter circuit, the oscillator means includes a crystal CRI which, in a preferred embodiment, is a Raltron AS 4.500-20-SMD available from Raltron Corporation, Miami, Fla. The output of crystal CR1 is connected to feedback resistor R1 and signal resistor R2. An invertor A1 and a bias resistor R3 are connected across the input of the crystal CR1 and the resistor R1. In a preferred embodiment, the invertors can be 7411C04 type inverters available from Philips Semiconductors, Sunnyvale, Calif. The output of the oscillator provides two inputs into two circuits. The first input is through resistor R1 and an invertor A2 into a connector. In a preferred embodiment, the connector is a J3 connector and the input is into pin 6 of the J3 connector. Pin 1 of the J3 connector is powered while pins 3 and 7 are set to ground. The second input is through resistor R2 into an analog gate U1. In a preferred embodiment, the analog gate U1 is a DG 601DY available from Maxim Corp., Sunnyvale, Calif. and the input is into the S1 and S2 input pins. Pins 4 of the J3 connector is connected to the analog gate through a pull-up resistor R4. Pin 5 of the J3 connector is input into the IN1 pin of the analog gate U1. This controls whether the signal proceeds through gates S1 and S2 or just through gate S2.

The output of analog gate U1 is input through a highpass filtering capacitor C1 into the base of an n-p-n transistor Q1. The collector of transistor Q1 is connected to a power source while the emitter is connected to the ultrasonic transmitter UT and to ground through buffer resistor R5. The ultrasonic transmitter UT also is grounded. A pair of bias resistors R6 and R7 are connected across the collector of transistor Q1 and ground, with the base connected to the junction of resistor R6 and resistor R7.

In operation, the signal to be selected is determined on pin 5 of the J3 connector. When the primary and test signals are desired, the SI pin of analog gate U1 is selected by pulling pin 5 low. When the test signal only is desired, the SI pin of analog gate U1 is selected by pulling pin 5 high. The selected signal is output from analog gate U1, high pass filtered by capacitor C1, and input into transistor Q1. Emitter follower transistor Q1 matches the relatively high-output impedance of the analog gate to relatively low impedance of the ultrasonic transmitter UT which electrically is on the order of 20 ohms in series with 1000 pF.

Referring now to the receiver circuit, an ultrasonic receiver UR is provided which receives the ultrasonic signal from the ultrasonic transmitter UT in the IV tube. The ultrasonic receiver UR is connected through capacitor C3 into the base of an n-p-n transistor Q2 and to ground. The input into transistor Q2 is limited by back-to-back diodes D1, D2 which prevent burnout if any transient signals are present. Transistor Q2 has a bandpass set by capacitor C3 and capacitor C4 connected in parallel with resistor R10. Resistors R8 and R9 set the gain of transistor Q2. A pair of resistors R11 and R12 are connected across the supply to bias transistor Q2, with the base connected to the junction of resistors R11 and R12.

The signal is buffered through an n-p-n transistor Q3, the base of which is connected to the collector of transistor Q2 through bleeder resistor R13 to prevent instability. The collector of transistor Q3 is connected to the power source while the emitter is connected to ground through resistor R14. The signal is provided from the emitter of transistor Q3 to the input of filter F1 through capacitor C5. A small gain is provided by a matching network consisting of resistor R15 in parallel with capacitor C7. The output of filter F1 is input into the receiver/demodulator U2 via capacitor C8 which also is optimized for match. A few db of gain is thus realized. The receiver/demodulator U2 electronically mixes the primary signal to an intermediate signal frequency. The mixing signal is provided by a second crystal local oscillator CR2 along with capacitors C9 and C10. The output of gilbert cell oscillator CR2 is connected to the receiver/demodulator U2 through capacitor C11 which forms the tank circuit.

The receiver/demodulator U2 signals include signal conditioning means and filtering means to amplify the desired signal via the mixer output, on pin 20, through bandpass filter F2 to pin 18, which amplifies the somewhat band limited signal and then through filter F3 to pin 14 which further amplifies the bandlimited signal. Via an internal feedback means, the received signal strength indicator ("RSSI") output on pin 7 represents a linear output for a logarithmic input appearing at the signal input port on pin 1 of receiver/demodulator U2. The RSSI signal is amplified by an internal operational amplifier in the receiver/demodulator U2 combined with resistors R16, R17 and rheostat VR1. After proper conditioning, the RSSI signal is provided to an A/D converter in the pump microprocessor. Thus, the pump microprocessor utilizes the RSSI signal which represents a linear output of the logarithmic change in signal level in determining whether an air or a liquid is in the IV tube.

Figure 17:
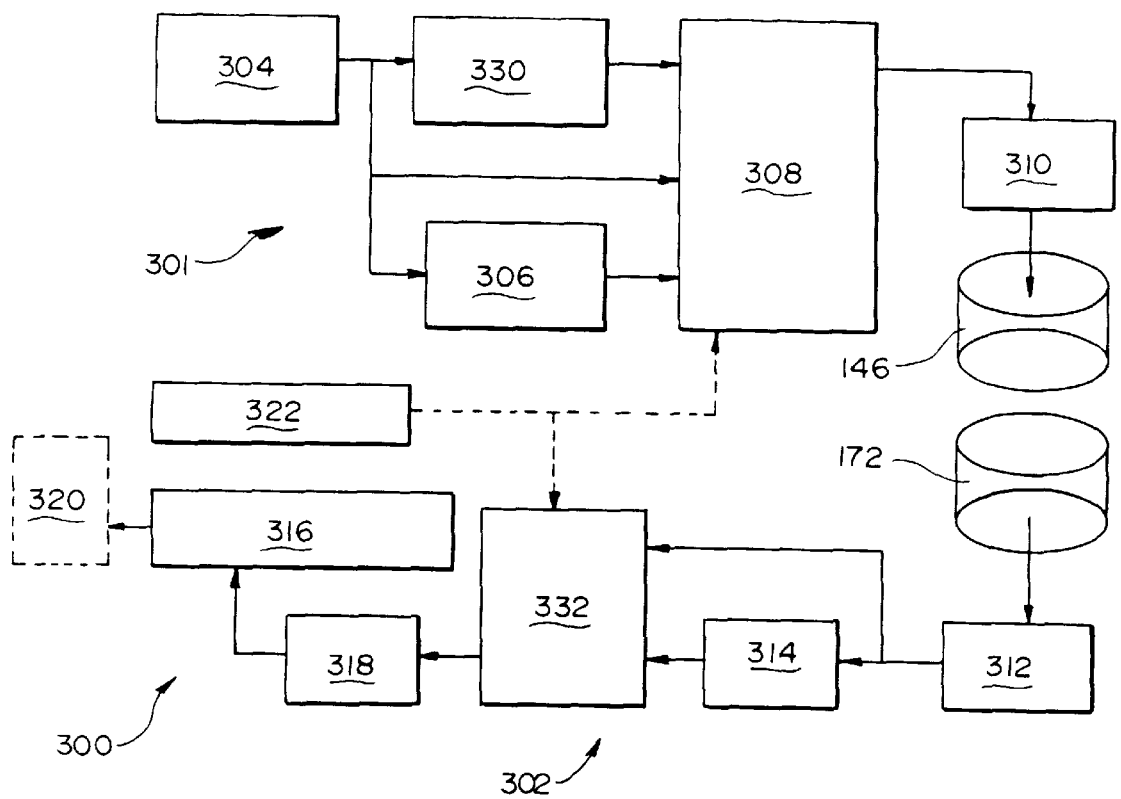
FIG. 17 is a block diagram of an alternative embodiment of an air detector circuit constructed in accordance with the principles of the present invention.

Referring now to FIG. 17, a second preferred embodiment of a circuit 300 for the air sensor is seen in the block diagram. The circuit includes both a transmitter circuit 301 and a receiver circuit 302. The transmitter circuit 301 includes means for generating an oscillation 304 which, in a preferred embodiment, is a 4.5 MHz oscillator. The oscillator 304 provides the primary signal to the air sensor transmitter. The transmitter circuit 301 further includes divider means 330 which provide a second signal. In the alternative preferred embodiment, the additional divider means 330 divides the 4.5 MHz signal by 10 to derive a secondary 450 KRz signal. In order to provide a test to detect variations in the receiver gain and to check the level of interference, a third signal is provided by a test means 306 for adding an attenuation to the primary signal to derive a test signal as done in the first preferred embodiment.

The primary signal, the secondary signal, and the test signal are input into means for switching 308 which, in the preferred embodiment, is an analog gate switch. The switching means 308 selects one of the three signals to be provided to an ultrasonic transmitter 146. After a gain 310 is provided to the selected signal, the signal is applied to the ultrasonic transmitter 146.

The receiver circuit 302 includes an ultrasonic receiver 172 which is positioned to receive the ultrasonic signals transmitted from the ultrasonic transmitter 146. After a gain is applied by a preamp 312, if the primary signal has been selected, it is applied to a second means for switching 332 which, in a preferred embodiment, is an analog gate switch. If the secondary signal has been selected, it is applied to the switching means through a filter which, in a preferred embodiment, is a 4.5 MHz bandpass ceramic filter. The switch means 332 passes the selected signal through a filter 318 which, in a preferred embodiment, is a 450 KHz bandpass ceramic filter, to a receiver demodulator 316. In a preferred embodiment, this receiver/demodulator is a Signetics SA 637 available from Signetics Corporation, Sunnyvale, Calif. The receiver/demodulator 316 converts the signal from the ultrasonic receiver into a calibrated output direct current. This signal is then input into an A/D converter 320, which provides a digital signal representative of the radio frequency signal received at the ultrasonic receiver.

The present invention allows two modes of operation to exist singly or in a combined fashion which takes advantage of the inherent design of the crystal. The thickness of the crystal is chosen to optimize the first mode of operation which is referred to as the "thickness mode" of resonance. The diameter of the crystal is chosen carefully to optimize the second mode of operation which is referred to as the "radial mode" of resonance. In the preferred embodiment, the thickness mode of resonance is 4.5 MHz while the area mode of resonance is 450 KHz. Each mode of resonance has unique properties that allow measurements that singly cannot be performed.

Figure 18:
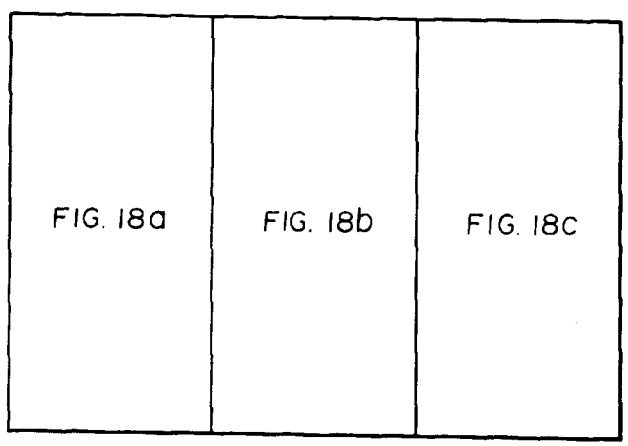
FIG. 18 is a schematic diagram of an alternative embodiment of an air detector circuit constructed in accordance with the principles of the present invention.
Figure 18A:
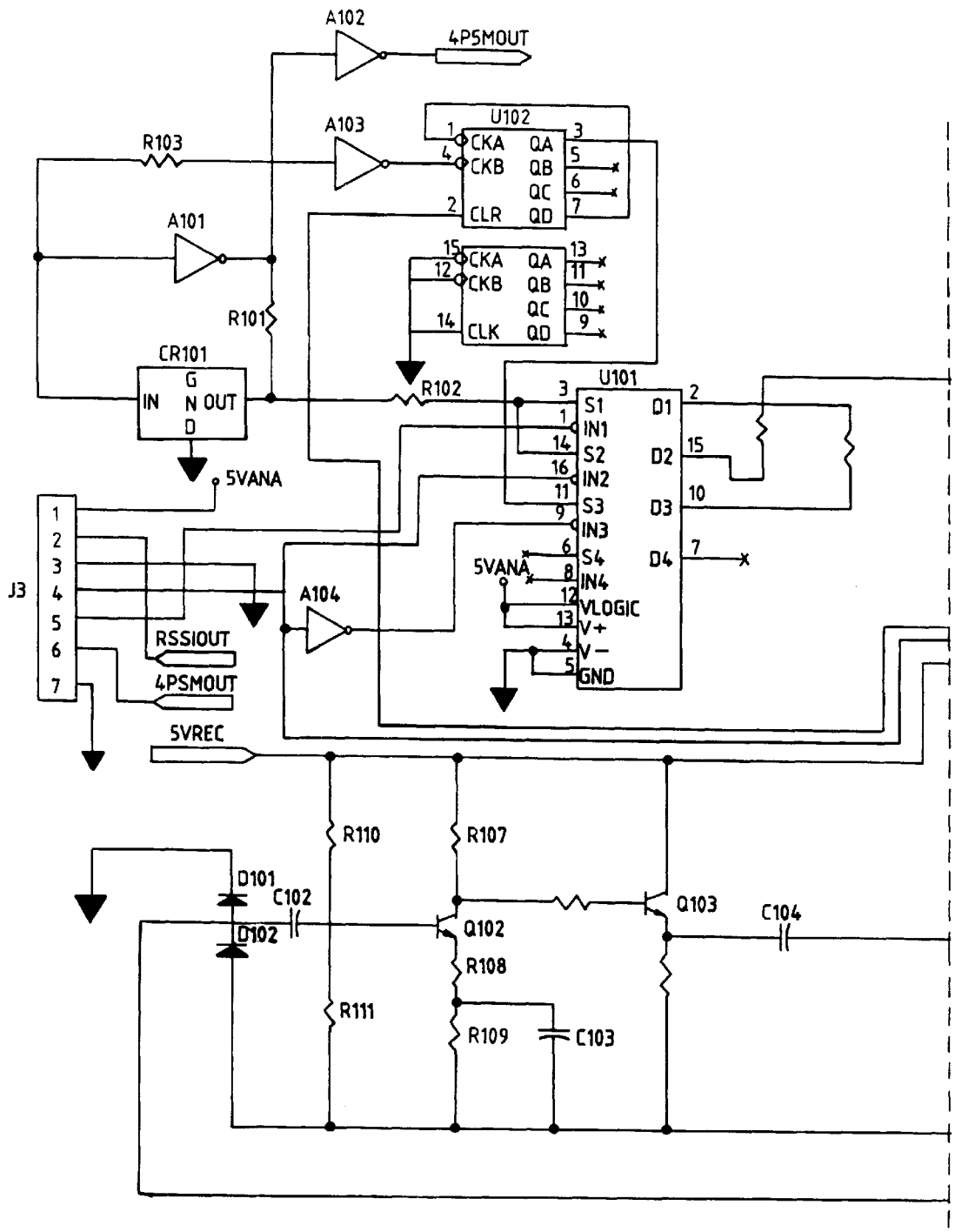
Figure 18B:
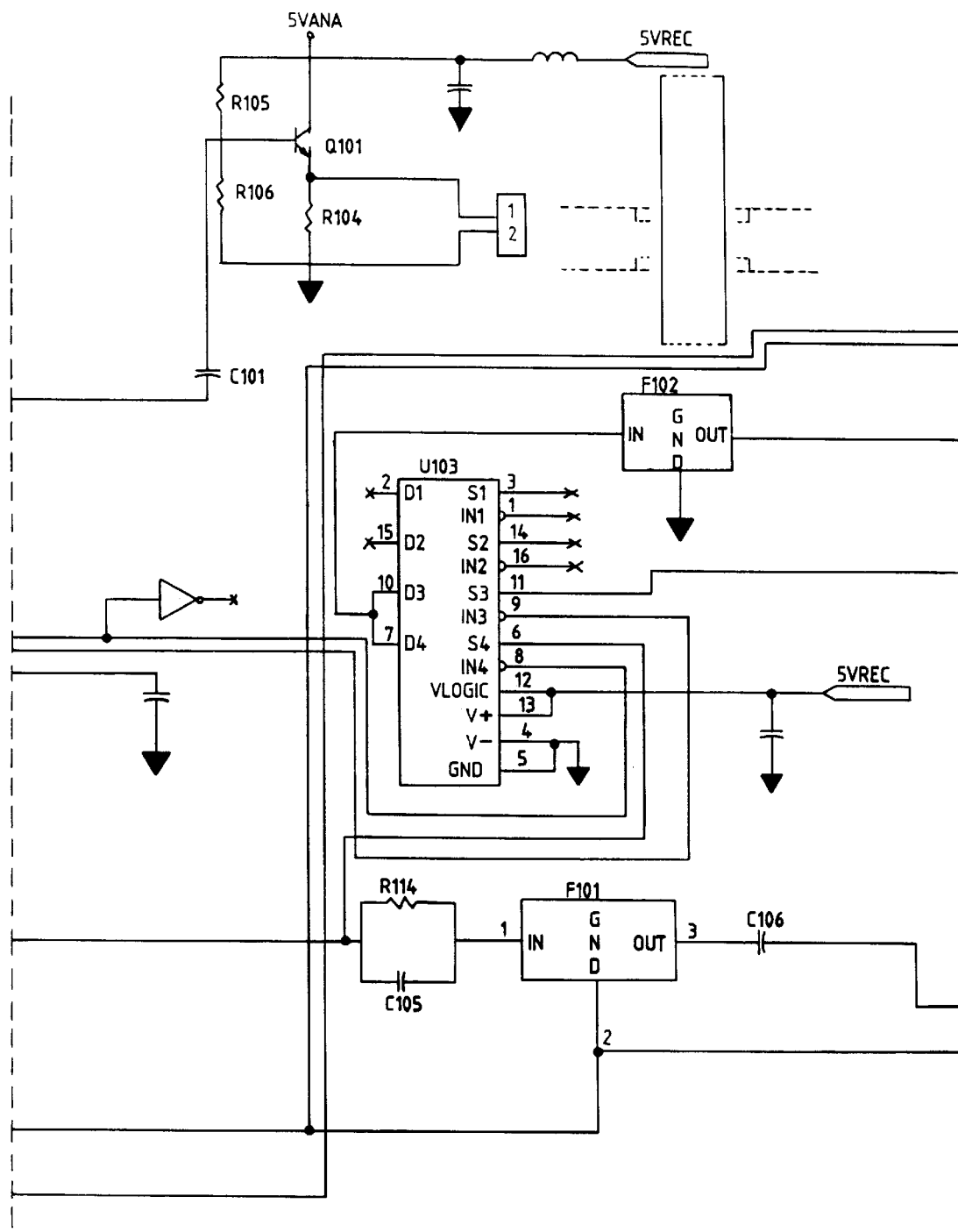
Figure 18C:
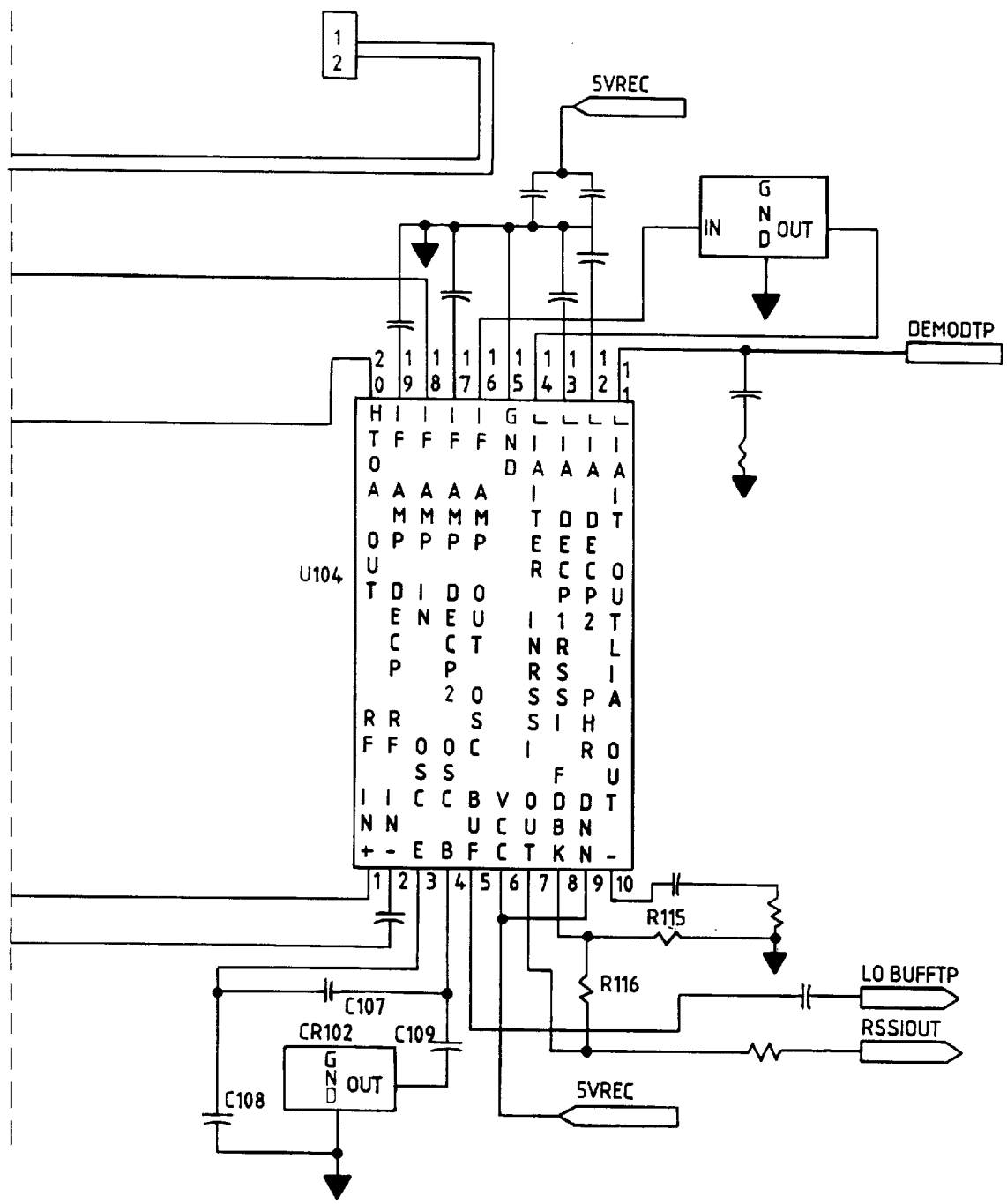

Referring now to FIG. 18, a schematic of the preferred circuit for the second embodiment of the air sensor is seen. Referring first to the transmitter circuit, the oscillator means includes a crystal CR101 which, in a preferred embodiment, is a Raltron AS 4.500-20-SMD available from Raltron Corporation, Miami, Fla. The output of crystal CR101 is connected to resistor R101 and feedback resistor R102. An invertor A101 and a resistor R103 are connected across the input of the crystal CR101 and the resistor R101. The output of the oscillator provides three inputs into three circuits. The first input is through resistor R101 and an invertor A102 into a connector for use by other pump circuitry. In a preferred embodiment, the connector is a J3 connector and the output is into pin 6. Pin 1 of the J3 connector is powered while pins 3 and 7 are set to ground. The second input is through resistor R102 into an analog gate U101. In a preferred embodiment, the analog gate U101 is a DG 601DY available from Maxim Corporation, Sunnyvale, Calif. and the input is into the S1 and S2 pins. Pin 4 of the J3 connector is input into the IN2 pin while pin 5 is input into the IN1 pin of the analog gate U101. The third input is through invertor A103 into a divider U102. In the preferred embodiment, the divider U102 is a 74 HC 390 counter available from Texas Instruments, Dallas, Tex.

The output of divider U102 is connected to pin S3 of the analog gate U101. The output of analog gate U101 is input through high pass capacitor C101 into the base of an n-p-n transistor Q101. The collector of transistor Q101 is connected to a power source while the emitter is connected to the ultrasonic transmitter UT and to ground through resistor R104. The ultrasonic transmitter UT also is grounded. A pair of resistors R105 and R106 are connected across power and ground whose common terminal is providing bias to the base of transistor Q101.

In operation, the signal to be selected is determined through the J3 connector. When the primary and test signals are desired, the S1 pin path of analog gate U101 is selected by setting pin 5 of the J3 connector high. When the test signal is desired, the S2 pin of analog gate U101 is selected. To achieve the secondary signal, the signal from crystal CR101 is buffered by invertor A103 and input into divider U102. The output of divider U102 is input into analog gate U101, When the primary signal is selected, divider U102 and the S3 pin of analog gate U101 are inhibited by the input of the J3 connector pin 5 low to analog gate U101 through invertor A104. This eliminates any possibility of leaks from the secondary signal to the primary signal. If present, a small artifact signal from the primary signal to the secondary signal is filtered out by the receiving circuit. As described in detail below, the select signals also are input into the receiver circuit. To select the secondary signal, pins 5 and pin 4 of the J3 connector are set high to enable the S3 pin and to inhibit the S1 and S2 pins of the analog gate U101.

The selected signal is output from analog gate U101, filtered by capacitor C101, and input into transistor Q101. Transistor Q101 matches the relatively high output impedance of the analog gate to relatively low impedance of the ultrasonic transmitter UT as previously described.

Referring now to the receiver circuit, an ultrasonic receiver UR is provided which receives the ultrasonic signal from the ultrasonic transmitter UT through the IV tube. The ultrasonic receiver UR is connected through capacitor C102 into the base of an n-p-n transistor Q102 and to ground. The input into transistor Q102 is limited by back-to-back diodes D101, D102 which prevent burnout if any transient signals are present. Transistor Q102 has a bandpass set by capacitor C102 and capacitor C103 connected in parallel with resistor R109. Resistors R107 and R108 set the gain of transistor Q102. A pair of resistors R110 and R111 are connected across the power and ground whose common connection bias the base of transistor Q102.

The signal is buffered through an n-p-n transistor Q103, the base of which is connected to the collect or of transistor Q102 through bleeder resistor R112 to provide stability. The collector of transistor Q103 is connected to a power source while the emitter is connected to ground through resistor R113. The signal is provided from the emitter of transistor Q103 to the input of filter F101 through capacitor C104. A small gain is provided by a matching network consisting of resistor R114 in parallel with capacitor C105. The output of filter F101 is input into the receiver/demodulator U104 via matching capacitor C106.

The signal also is provided from the emitter of transistor Q103 via capacitor C104 to a receiver analog gate U103. In a preferred embodiment, analog gate U103 is a DG 601DY available from Maxim Corp., Sunnyvale, Calif. and the input is into the S4 pin. The control signal from the J3 connector, pin 4, is provided through invertor A104 to the IN3 pin of analog gate U103. The output of analog gate U103 is input into a filter F102, the output of which is input into the receiver/demodulator U104. This forms the direct though path for the second signal which by passes the filter F101.

When the primary signal is selected, the control signal received by the receiver circuit sends the signal through filter F101 to receiver/demodulator U104. When the secondary signal is selected, the control signal received by the receiver circuit routes the signal into analog gate U103, through filter F102, to the receiver/demodulator U104. The receiver/demodulator U104 standardizes both signals to a secondary signal frequency. To accomplish this, the primary signal is mixed with a mixing signal. A mixing local oscillator is provided by a second crystal CR102 along with capacitors C107 and C108. The frequency of crystal CR102 is selected to achieve a combined frequency for the primary signal equal to the frequency of the secondary signal. The output of crystal CR102 is connected to the receiver/demodulator U104 through capacitor C109. The receiver/demodulator U104 signals include signal conditioning means and filtering means to amplify the desired signal via the mixer output, on pin 20, through bandpass filter F102 to pin 18, which amplifies the somewhat bandlimited signal and then through filter F3 to pin 14 which further amplifies the bandlimited signal. Via an internal feedback means, the received signal strength indicator ("RSSI") output on pin 7 represents a linear output for a logarithmic input appearing at the signal input port on pin I of receiver/demodulator U2. The RSSI signal is amplified by an internal operational amplifier in the receiver/demodulator U104 combined with resistors R115, R16. The RSSI signal is provided to an A/D converter in the pump microprocessor. Thus, the pump microprocessor utilizes the RSSI signal which represents a linear output of the logarithmic change in signal level in determining whether an air or a liquid is in the IV tube. In this embodiment, the gain provided by resistors R115 and R116 is fixed as opposed to the first embodiment in which the gain was variable.

It should be understood that various changes and modifications to the preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

What is claimed is:

1. An infusion pump comprising:

means for applying pumping action to a liquid flow-through tube;

an ultrasonic transmitter for transmitting ultrasonic signals;

an ultrasonic receiver for receiving ultrasonic signals, the ultrasonic transmitter and the ultrasonic receiver being separated by the liquid flow-through tube;

circuit means in communication with the ultrasonic transmitter for generating a transmitted signal to activate the ultrasonic transmitter;

circuit means in communication with the ultrasonic receiver for detecting received signals; and means in communication with the circuit means for detecting received signals and utilizing a logarithmic change in signal level for detecting whether the received signal is indicative of air or liquid in the liquid flow-through tube.

2. An apparatus for detecting excessive air in a liquid flow-through tube comprising:

an ultrasonic transmitter for transmitting ultrasonic signals;

an ultrasonic receiver for receiving ultrasonic signals, the ultrasonic transmitter and the ultrasonic receiver being separated by the liquid flow-through tube;

circuit means in communication with the ultrasonic transmitting for generating a first primary transmitting signal and second primary transmitting signal to activate the ultrasonic transmitter;

circuit means in communication with the ultrasonic receiver for detecting received signals; and means in communication with the circuit means for determining whether the received signal is indicative of air or liquid in the liquid flow-through tube.

3. The apparatus of claim 2 wherein the at least two signals include a primary signal and a test signal.

4. The apparatus of claim 2 wherein the ultrasonic transmitter includes an ultrasonic crystal and the first primary transmitting signal is based on the frequency of the thickness of the ultrasonic crystal.

5. The apparatus of claim 2 wherein the determining means utilizes a logarithmic change in signal level for determining whether the received signal is indicative of air or liquid in the tube.

6. An apparatus for detecting excessive air in a liquid flow-through tube comprising:

an ultrasonic transmitter for transmitting ultrasonic signals;

an ultrasonic receiver for receiving ultrasonic signals, the ultrasonic transmitter and the ultrasonic receiver being separated by the liquid flow-through tube;

circuit means in communication with the ultrasonic transmitter for generating a transmitting signal to activate the ultrasonic transmitter;

circuit means in communication with the ultrasonic receiver for detecting received signals; and means in communication with the circuit means for detecting received signals and which utilizes a logarithmic change in signal level for determining whether the received signal is indicative of air or liquid in the liquid flow-through tube.

7. The apparatus of claim 6 wherein the generating circuit means generates at least two transmitting signals to actuate the ultrasonic transmitter.

8. The apparatus of claim 7 wherein the ultrasonic transmitter includes an ultrasonic crystal and the first transmitter signal is based on the frequency of the thickness of the ultrasonic crystal.

* * * * *